US006805867B1

(12) United States Patent
Saif et al.

(10) Patent No.: US 6,805,867 B1
(45) Date of Patent: Oct. 19, 2004

(54) BOVINE ROTAVIRUS GENES

(75) Inventors: Linda J. Saif, West Salem, OH (US); Anil Parwani, Cleveland Heights, OH (US); Kyeong-Ok Chang, Wooster, OH (US); Wonyong Kim, Wooster, OH (US); Kathy Gadfield, Dalton, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 09/232,338

(22) Filed: Jan. 15, 1999

Related U.S. Application Data

(62) Division of application No. 08/671,978, filed on Jun. 28, 1996, now Pat. No. 5,959,093.

(51) Int. Cl.[7] .......... A61K 39/15

(52) U.S. Cl. .......... 424/215.1; 424/186.1; 424/204.1

(58) Field of Search .......... 424/215.1, 186.1, 424/204.1

(56) References Cited

U.S. PATENT DOCUMENTS 5,298,244 A 3/1994 Redmond et al.

OTHER PUBLICATIONS

Tsunemitsu, H., et al., 1996, "Sequence comparison of the VP7 gene encoding the outer capsid glycoprotein among animal and human group C rotaviruses", Arch. Virol. 141:705–713.*

Tsunemitsu, H., et al., 1992, "Evidence of serologic diversity within Group C rotaviruses", J. Clin. Microbiol. 30(11):3009–3012.*

"Characterization of Field Strains of Group A bovine Rotaviruses by Using a Polymerase Chain Reaction–Generated G and P Type–Specific cDNA Probes" by Parwani, et al., *Journal of Clinical Microbiology*, vol. 31, No. 8, Aug. 1993, pp. 2010–2015.

"Detection and differentiation of bovine group A rotavirus stereotypes using polymerase chain reaction–generated probes to the VP7 gene" by Parwani, et al., *J Vet Diagn Invest* 4:148–158 (1992).

"Development of cDNA Probes for Typing Group A Bovine Rotaviruses on the Basis of VP4 Specificity" by Parwani, et al., *Journal of Clinical Microbiology*, vol. 30, No. 10, Oct. 1992, pp. 2717–2721.

"Characterization of Virus–Like Particles Produced by the Expression of Rotavirus Capsid Proteins in Insect Cells" by Crawford, et al., *Journal of Virology*, vol. 68, No. 9, Sep. 1994, pp. 5945–5952.

"Sequence comparison of the VP7 gene encoding the outer capsid glycoprotein among animal and human group C rotaviruses" by Tsunemitsu, et al., *Archives of Virology*, (1996) 141:705–713.

"Isotype–specific antibody responses to rotavirus and virus proteins in cows inoculated with subunit vaccines composed of recombinant SA11 rotavirus core–like particles (CLP) or virus–like particles (VLP)" by Fernandez, et al., Thu Jul. 4 14:00:02 1996: JVAC: 415: tx1.

"Isolation, Characterization, and Serial Propagation of a Bovine Group C Rotavirus in a Monkey Kidney Cell Line (MA104)" by Tsunemitsu, et al, *Journal of Clinical Microbiology*, vol. 29, No. 11, Nov. 1991, pp. 2609–2613.

"A survey of G6 and G10 serotypes of group A bovine rotaviruses from diarrheic beef and dairy calves using monoclonal antibodies in ELISA" by Lucchelli, *J Vet Diagn Invest* 6:175–181 (1994).

"Molecular and serologic characterization of a group A bovine rotavirus with a short genome pattern" by Parwani, et al, *J Vet Diagn Invest*, 7:255–261 (1995).

"Comparative Nucleotide and Deduced Amino Acid Sequence Analysis of VP7 gene of G6 IND and G10 2292B field group A BRV strains" by Parwani, et al., Genbank Accession No. U15000, Feb. 16, 1996.

"Sequence Analysis of VP3 and VP4 genes of a bovine group C rotavirus: molecular evidence for a new P type" by Jiang, et al., Genbank Accession No. BRU26551, Jun. 5, 1996.

* cited by examiner

*Primary Examiner*—Laurie Scheiner
*Assistant Examiner*—Jeffrey S. Parkin
(74) *Attorney, Agent, or Firm*—Calfee, Halter & Griswold LLP

(57) ABSTRACT

The present invention provides the genes encoding the following BRV proteins: for group A, the VP4 and VP7 proteins of the Indiana (IND) strain, and the VP7 protein of the 2292B strain; for group B, the VP7 protein of the WD653 strain; for group C, the VP4 and VP7 proteins of the Shintoku strain. The genes are useful for producing nucleic acid probes which are complementary to the VP7 and VP4 genes. Such probes are useful for detecting the presence of group A,B, and C BRV in fecal samples from diarrheic calves and for determining the serotype of the BRV field isolates. The genes are also useful for producing partial length nucleic acid probes which are complementary to hypervariable regions of the VP4 and VP7 genes.

The present invention also relates to partially purified VP2, VP4, VP6 and VP7 proteins of the IND strain and VP4 and VP7 of the 2292B strain, the partially purified VP7 protein of the WD653 strain, and partially purified VP2, VP4 and VP7 proteins of the Shintoku strain. The present invention also relates to recombinant virus-like particles (VLPs) which comprise one or more of the VP2, VP4, VP6, and VP7 proteins of the BRV strains IND, 2292B, CR, WD653, and Shintoku.

8 Claims, 14 Drawing Sheets

Fig. 1

```
   1  GGCTTTAAAA GCGAGAATTT CCGTTTGGCT AGCGGTTACG TCCTTTTAAT GTATGGTATT
  61  GAATATACCA CAATTCTAAT CTTCTTGACA TCAGTTACAT TGCTAAATTA TATCTTAAAA
 121  TCAATAACAA GAGTAATGGA CTATATAATT TACAGATTTC TGCTTATAGT GGTAATCTTG
 181  GCCACCATGA TAAATGCGCA TAATTATGGA GTGAATTTGC CAATTACAGG TTCAATGGAT
 241  ACTGCATACG CAAATTCATC GCAAAGTGAG CCATTTTTAA CATCAACTCT TTGTTTGTAT
 301  TATCCTGTTG AGGCATCAAA CGAAATAGCT GATACTGAAT GGAAAGATAC CTTATCACTA
 361  ATGTTCTTGA CAAAAGGATG GCCAACAGGA TCGGTGTACT TTAAAGAATA TACTGATATA
 421  GCGGCTTTTT CAGTAGAACC ACAGCTGTAC TGTGATTATA ATTTAGTTTT AATGAAATAT
 481  GATTCTACAC AGGAACTAGA TATGTCTGAA TTAGCCGATC TTATACTGAA CGAATGGCTG
 541  TGCAATCCCA TGGACATAAC GTTGTATTAT TATCAGCAGA CTGATGAAGC AAATAAATGG
 601  ATATCGATGG GCTCTTCTTG CACAGTCAAA GTGTGTCCAT TAAATACGCA GACACTTGGT
 661  ATTGGATGTC TAATAACTAA TCCAGACACG TTTGAAACAG TTGCGACAAC GGAGAAGTTG
 721  GTGATTACAG ATGTTGTAGA TGGTGTCAAC TATAAGTTAA ACGTCACAAC AGCAACGTGT
 781  ACCATACGCA ACTGTCAAAA ATTAGGACCA AGGGAGAATG TAGCTGTCAT ACAGGTAGGC
 841  GGCGCGAATA TTTTAGACAT CACAGCTGAT CCAACAACAT CACCACAGAC AGAGAGAATG
 901  ATGCGAATAA ATTGGAAAAA ATGGTGGCAA GTATTCTACA CAGTGGTGGA TTATGTCAAT
 961  CAAATAATTC AAACGATGTC CAAAAGATCT AGATCGCTTA ACTCGTCAGC GTTCTATTAC
1021  AGAGTATAGG TGCATGTTAG ATTAGAGTTG TATGATGTGA CC
```

Fig. 2

```
   1  GGCTTTAAAA GCGAGAATTT CCGTTTGGCT AGCGGTTAGC TCCTTTTAAT GTATGGTATT
  61  GAATATACCA CATTCCTAAT CTACTTGATA TCAATTATAT TACTTAATTA CATATTAAAA
 121  AGTATAACTA GAATGATGGA GTACATAATT TACAAATTTT TGCTTATAGT CACAATTACT
 181  TCAATTGTTG TTAATGCACA AAATTACGGT ATCAATTTAC CAATAACCGG ATCAATGGAT
 241  ACATCATATG TGAATGCACC TAAAGATGAG CCATTTCTAA CGTCAACATT ATGTTTATAC
 301  TATCCAACAG AAGCTAGAAC AGAGATAAAC GATAATGAGA GGACAAGTAC GTTGTCGCAG
 361  CTGTTCTTAA CAAAGGGATG GCCGACTGGA TCCGTATACT TTAAAGAATA TGATGATATA
 421  GCTACTTTCT CAGTGGATCC ACAACTGTAT TGTGACTATA ATATAGTTCT GATGAGATAT
 481  AATTCGAGCC TAGAACTTGA TATGTCGGAA TTAGCAAATC TAATATTGAA TGAATGGCTA
 541  TGCAATCCAA TGGACATTAC ATTGTATTAT TACCAACAGA CAGACGAGGC AAACATATGG
 601  ATAGCAATGG GACAATCATG TACTATAAAA GTGTGTCCAT TGAATACCCA AACGCTAGGA
 661  ATAGGATGTC AGACTACACA TACTGGAACG TTTGAAGAGG TCGCAACGGC TGAAAAATTG
 721  GTAATTACTG ATGTAGTTGA CGGCGTAAAT CACAAACTAG ATGTTACTAC TGCGACCTGT
 781  ACTATTAGAA ATTGTAAGAA ATTGGGGCCA AGAGAAAATG TAGCAGTGAT ACAAGTGGGT
 841  GGTGCTGATA TCCTTGACAT AACATCTGAT CCGACGACTA ATCCACAAAC TGAATGGATG
 901  ATGCGAATAA ATTGGAAGAA ATGGTGGCAA GTGTTCTACA CTATAGTTGA TTACGTGAAC
 961  CAAATTGTGC AAGCAATGTC CAAGAGGTCC AGATCACTGA ATTCAGCAGC GTTTTATTAT
1021  AGAGTGTAGA TATTATGTAG GTTAGAGTTG TATGATGTGA CC
```

Fig. 3

```
   1  GGCATTTAAA AAAGAAGGAG CTGTCTGACA AACTGGTCTT CTTTTTAAAT GGTTTGTACA
  61  ACATTGTACA CCGTTTGCGT GATTCTCTGC ATTCTGCTAA TGTATATAAT ACTGTTCAGA
 121  AAAATGATTC ATTTTCTAAT CGACTTGTCA CTTATTGCTT TTGTAATATC AAGTTGCATC
 181  AGACTGTCTA ATGCTCAGTT TTTTGCTAAT GACATGCTTT ATAATGGTAA TGTTGAAGGT
 241  GTAATTAATA CGACAAATAT TTTTAATGTT GAATCTCTTT GCATTTACTT TCCAAATTCT
 301  GCAGTGGGGC GACCTGGTCC AGGGAAGAGT GATGGTTTGA TTAATGACAA CAACTACGCT
 361  CAAACACTAG CAGTTCTTTT TGAAACAAAA GGATTTCCTA AAGGATCAGT GAATTTTAAT
 421  ACTTATACTA AAATATCTGA CTTTATAAAT TCAATTGAAA TGACATGTTC TTATAACATA
 481  GTTATAATTC CTGAAACTCT AGCTAATTCT GAAACGATTG AACAAGTAGC TGAGTGGGTC
 541  CTTAATGTGT GGAAATGTGA CAATATGAAT GTGGATATTT ATACTTATGA ACAAATAGGG
 601  AAAGACAATT TTTGGGCGGC ATTTGGTGAA GATTGTGATG TTGCGGTATG TCCACTAGAC
 661  ACAACAATGA ATGGTATCGG ATGTACGCCA GCAAGTACAG AGACGTATGA AGTACTATCA
 721  AATGACACTC AGTTGGCCCT TATAGATGTA GTGGATAATG TGAAACATAG AATACAACTG
 781  AATCAAGTAA CGTGTAAATT GAGAAATTGT GTGAAAGGTG AAGCAAGACT TAACACAGCG
 841  ATTGTAAGAA TTTCGAACTT GTCCAGTTTT GATAATTCAT TGTCACCATT GAATAATGGG
 901  CAGAAGACAA GATCCTTTAA AATTAATGCG AAGAAATGGT GGAAAATATT CTATACTATA
 961  ATTGATTACA TTAATACATT CATACAATCT ATGACACCTA GGCACAGAGC CATTTATCCC
1021  GAAGGATGGA TGCTGAGATA TGCGTAAACG AGATTATGTG GCT
```

Fig. 4

| | | | | | |
|---|---|---|---|---|---|
| 1 | AAATAATCAG | AGATGGCGTTC | GCTGCTTGTG | CAAAAGCTCA | ATTAGTGATT |
| 51 | ACACCAATCA | GCAATCCGGA | GATTTGTGTG | CTGCACGCTA | GTACTGGAAT |
| 101 | GTGGATAGTT | TCGGACGACA | ACTTTACAAA | TATTTTTGAA | ACGTATAATT |
| 151 | CAGTAACTCT | ATCCTTTTTA | CCGTATGATA | GCACCAACTA | TGATGTGATT |
| 201 | GATATTATAT | CTAAGAGAGA | TTATTCACTG | TGTCATATAT | TGGCAATAGA |
| 251 | TGTCATAAAG | CCTGAAATGG | ATTTTATTAC | GTTTCTTCAA | TCAAATAATG |
| 301 | AATGTTCAAA | ATATGCAGGG | CAGAAAATAG | ATTATCAAAA | ACTTTCAACA |
| 351 | AACGAAGAAT | GGTTTGTTTA | TTCAAAGAAT | TTGAAATTCT | GTCCACTATC |
| 401 | TGACAGCCTA | ATCGGATTGT | ATTGCGATAC | GCAGGTAAGT | GGTACGTATT |
| 451 | TTCCATTATC | AGAGAATGAA | AAATACGATG | TTACGGATCT | ACCAGAGTTT |
| 501 | ACAGAAATGG | GTTACGTCTT | TTATTCGAAT | GATGACTTTT | ATATTTGTAA |
| 551 | ACGCATCAAT | GAGGATAATA | AATGGTCGAA | TTATCATCTT | TTTTACAGAG |
| 601 | AATACTCGGC | ATCAGGGACG | GTGTCAAGAG | CTATCAGTTG | GGACAACGTA |
| 651 | TGGACTGGTT | TCAAGACATT | CGCGCAGGTT | GTATATAAAA | TACTAGATAT |
| 701 | TTTTTTCAAC | AATAGAAGGA | ACTTTTTCTT | TATTGGCTTC | GGCCTACTCG |

Fig. 5

| | | | | | |
|---|---|---|---|---|---|
| 1 | AGCTTAAAAA | AGTCAGGATC | AATGGCGTCC | TCACTTTACC | GTCAGCTGAT |
| 51 | ATCCCAGAAC | TATTATTCAA | CTGGAAATGA | AATACTACTG | GATCAGCAAA |
| 101 | CAAACAAAAC | AACTGTTGAT | TATGTAGATG | CTGGGAATTA | CACATATGCC |
| 151 | CAGTTACCAC | CAACAACGTG | GGGAGCAGAG | TCGACATATG | AATCTGCATT |
| 201 | CAGCGCGCCA | GAGATAACTG | GACCATATAC | AAATACAGTC | ATAAAATTGA |
| 251 | GTGATCTATC | AGATTCGAAC | GTATGGGTAT | TATATATCAG | ACCAACTAGC |
| 301 | ACAGTTAAAT | TGCTTAAAAA | TGGACCAGAA | AGTTATAGTT | GGAACCTTGC |
| 351 | AGCATTTGAA | TTATGGTATG | GAAAGGCAAA | TACAACGGTT | ACATCAGATT |
| 401 | ACTATTCAGG | GATGACAAAT | TCTGAAAAAA | GTGTTGAGGT | AGATCATGAT |
| 451 | TCACTAGTAC | TATTTTGGAA | TGAAGGCTCA | ACAGCATTAA | GTAACAAAGT |
| 501 | GATCAATTTT | TCCTGGAATG | TTGGTGGCGT | GTTAATTAAA | CTAACAAGTA |
| 551 | ATACAAGGAT | AGACATATGC | ATGGCTAACA | TGGATAATTT | TACTAGTGAT |
| 601 | AGCTTCAATT | GGGAAGAATG | GACACATAAT | TTTCCTCGCA | GTGCGAGCAT |
| 651 | GAACATTTAT | ACTGATTACT | ACTTAGCTAG | TGTAGATCCA | TATAGTCAAA |
| 701 | TAAGAGCATT | ACAGCAACCA | ATAATAACAA | CTGTTGAAAT | GAAGATGGTG |
| 751 | AAAGTTAAGA | GAGAAGGATC | AATTAATGTA | GATGAAGTTG | TAAGTAAGGA |
| 801 | TTCATTATGG | CAAGAGGTAA | GGTACGTTAG | AGATATAACA | CTTCAGTGTA |
| 851 | AAATTGAGTC | TGAAGTTGTT | AAAGGTGGTG | GATGGGGTTA | TGACTATACT |
| 901 | AGCGTAGCCT | TTAAAACCAT | TAATCACACG | TACTCTTATA | CTAGAGCAGG |
| 951 | AGAGGCTGTT | AATGCGCACG | TTACAATTAG | TTTTAACAAT | TTGAAGGAAC |
| 1001 | GCTCATATGG | AGGGTCATTA | CCAACTGATT | TCAAAATTGG | ACGGTTCGAC |
| 1051 | ATAATAGACG | TTGATACATA | CATGTACATA | GATTATTGGG | ATGACTCAGA |
| 1101 | AATCTTTAAA | AATATGGTGT | ATGTGCGTGA | TTTGAGAGCT | GATATGGGTG |
| 1151 | GATTTAATTA | CTCGTCAGCC | ATGTCATACT | ACTTTAGAAT | TCCCGTTGGG |
| 1201 | CAGTATCCTG | GGTTGCATTC | ATCAGGAGTA | AGATTTACAT | ATGAGAGGAG |
| 1251 | TCTATTATCT | CAACAATTTA | CTGATCAGGT | AGCGCTTAAT | TCAATGAGAT |
| 1301 | TTGTGTTCAG | AGCAACATCA | TCAGATGGTT | GGTTTATGAC | AGCAGGAAAT |
| 1351 | ATAAATGCAA | GACGTATAGC | GTCTGGAACA | GGATTTGCAT | ATTCGGATGG |
| 1401 | TTATGTTACT | GAAACTGTTG | GGACGGTTTC | GTTTATATCA | TTAATTCCAA |
| 1451 | GCAATCCAAA | TTATCAGACA | CCAATAGCTT | CATCAAGTAC | AGTGAGAATG |
| 1501 | GATTTAGAAC | GGAAGATTAA | CGATCTACGT | AATGATTTCA | ATGAATTGGC |
| 1551 | TAGTTCTGTT | GCACTAGGTG | ACATACTATC | ACTAGCAATG | TCTCCATTGA |
| 1601 | CCTTTGCTAA | TCTACTTGAA | TCTGTTCCAG | CAATTGCATC | ATCTGTGAAA |
| 1651 | GATGTTGCGG | CAAACGTCAT | GAAAAAGTTT | AAAACGACGA | AAATGTTTAA |
| 1701 | AAAAGCTGCA | AAGCCAAAGT | ATAAGGAATA | TATTATCGGA | GACTTGCTAG |
| 1751 | AAGATGTGAC | AAATCTTCCA | AGAAGTACTA | CCGCAATGGA | TTTTGATGAT |
| 1801 | ATTACATCAG | CAGTAATGGT | TTCAACAACA | AACAGGTTGC | AGCTTACAGA |
| 1851 | TGTAGAAACG | CTGTCAGAAA | TTGTAGCCAG | ATCAGCAGAT | GATTTCATAC |
| 1901 | CCAATAGAGC | GTATAGAATG | | | |

Fig. 6

| | | | | | |
|---|---|---|---|---|---|
| 1 | MYGIEYTTIL | IFLTSVTLLN | YILKSITRVM | DYIIYRFLLI | VVILATMINA |
| 51 | HNYGVNLPIT | GSMDTAYANS | SQSEPFLTST | LCLYYPVEAS | NEIADTEWKD |
| 101 | TLSLMFLTKG | WPTGSVYFKE | YTDIAAFSVE | PQLYCDYNLV | LMKYDSTQEL |
| 151 | DMSELADLIL | NEWLCNPMDI | TLYYYQQTDE | ANKWISMGSS | CTVKVCPLNT |
| 201 | QTLGIGCLIT | NPDTFETVAT | TEKLVITDVV | DGVNYKLNVT | TATCTIRNCQ |
| 251 | KLGPRENVAV | IQVGGANILD | ITADPTTSPQ | TERMMRINWK | KWWQVFYTVV |
| 301 | DYVNQIIQTM | SKRSRSLNSS | AFYYRV | | |

Fig. 7

| | | | | | |
|---|---|---|---|---|---|
| 1 | MYGIEYTTFL | IYLISIILLN | YILKSITRMM | EYIIYKFLLI | VTITSIVVNA |
| 51 | QNYGINLPIT | GSMDTSYVNA | PKDEPFLTST | LCLYYPTEAR | TEINDNERTS |
| 101 | TLSQLFLTKG | WPTGSVYFKE | YDDIATFSVD | PQLYCDYNIV | LMRYNSSLEL |
| 151 | DMSELANLIL | NEWLCNPMDI | TLYYYQQTDE | ANIWIAMGQS | CTIKVCPLNT |
| 201 | QTLGIGCOTT | HTGTFEEVAT | AEKLVITDVV | DGVNHKLDVT | TATCTIRNCK |
| 251 | KLGPRENVAV | IQVGGADILD | ITSDPTTNPQ | TEWMMRINWK | KWWQVFYTIV |
| 301 | DYVNGIVQAM | SKRSRSLNSA | AFYYRV | | |

Fig. 8

| | | | | | |
|---|---|---|---|---|---|
| 1 | MVCTTLYTVC | VILCILLMYI | ILFRKMIHFL | IDLSLIAFVI | SSCIRLSNAO |
| 51 | FFANDMLYNG | NVEGVINTTN | IFNVESLCIY | FPNSAVGRPG | PGKSDGLIND |
| 101 | NNYAQTLAVL | FETKGFPKGS | VNFNTYTKIS | DFINSIEMTC | SYNIVIIPET |
| 151 | LANSETIEQV | AEWVLNFWKC | DNMNVDIYTY | EQIGKDNFWA | AFGEDCDVAV |
| 201 | CPLDTTMNGI | GCTPASTETY | EVLSNDTQLA | LIDVVDNVKH | RIQLNOVTCK |
| 251 | LRNCVKGEAR | LNTAIVRISN | LSSFDNSLSP | LNNGQKTRSF | KINAKKWWKI |
| 301 | FYTIIDYINT | FIQSMTPRHR | AIYPEGWMLR | YA | |

Fig. 9

| | | | | | |
|---|---|---|---|---|---|
| 1 | MAFIASRLAA | CAKAQLVITP | ISNPEICVLH | ASTGMWIVSD | DNFTNIFETY |
| 51 | NSVTLSFLPY | DSTNYDVIDI | ISKRDYSLCH | ILAIDVIKPE | MDFITFLQSN |
| 101 | NECSKYAGQK | IDYQKLSTNE | EWFVYSKNLK | FCPLSDSLIG | LYCDTQVSGT |
| 151 | YFPLSENEKY | DVTDLPEFTE | MGYVFYSNDD | FYICKRINED | NKWSNYHLFY |
| 201 | REYSASGTVS | RAISWDNVWT | GFKTFAQVVY | KILDIFFNNR | RNPGPRAM |

Fig. 10

| | | | | | |
|---|---|---|---|---|---|
| 1 | MASSLYRQLI | SQNYYSTGNE | ILLDQQTNKT | TVDYVDAGNY | TYAQLPPTTW |
| 51 | GAESTYESAF | SAPEITGPYT | NTVIKLSDLS | DSNVWVLYQK | PTSTVKLLKN |
| 101 | GPESYSWNLA | AFELWYGKAN | TTVTSDYYSG | MTNSEKSVEV | DHDSLVLFWN |
| 151 | EGSTALSNKV | INFSWNVGGV | LIKLTSNTRI | DICMANMDNF | TSDSFNWEEW |
| 201 | THNFPRSASM | NIYTDYYLAS | VDPYSQIRAL | QQPIITTVEM | KMVKVKREGS |
| 251 | INVDEVVSKD | SLWQEVRYVR | DITLQCKIES | EVVKGGGWGY | DYTSVAFKTI |
| 301 | NHTYSYTRAG | EAVNAHVTIS | FNNLKERSYG | GSLPTDFKIG | RFDIIDVDTY |
| 351 | MYIDYWDDSE | IFKNMVYVRD | LRADMGGFNY | SSAMSYYFRI | PVGQYPGLHS |
| 401 | SGVRFTYERS | LLSQQFTDQV | ALNSMRFVFR | ATSSDGWFMT | AGNINARRIA |
| 451 | SGTGFAYSDG | YVTETVGTVS | FISLIPSNPN | YQTPIASSST | VRMDLERKIN |
| 501 | DLRNDFNELA | SSVALGDILS | LAMSPLTFAN | LLESVPAIAS | SVKDVAANVM |
| 551 | KKFKTTKMFK | KAAKPKYKEY | IIGDLLEDVT | NLPRSTTAMD | FDDITSAVMV |
| 601 | STTNRLQLTD | VETLSEIVAR | SADDFIPNRA | YRMIEDGMVH | EATPNGVFSY |
| 651 | DLATLQQRNF | DMEKFMQLAS | KSPVISAIVD | FATLKAMRDT | YGVSTDIMYK |
| 701 | LVASDAPTIV | SFINNNNPLI | RNRIEGLLRQ | CRI | |

Fig. 11

| | | | | | |
|---|---|---|---|---|---|
| 1 | GGCTATAAAA | TGGCTTGGCT | CATATACAGA | CAGCTGCTCG | ATCATTCTTA |
| 51 | CGCAGTAGAT | TTATCTGATG | AGATACAGTC | AGTTGGATCA | GAGAAGAACC |
| 100 | AACGCGTTAC | AGTGAATCCA | GGACCATTTG | CGCAGACAGG | ATATGCGCCA |
| 151 | GTGAACTGGG | GGCCCGGTGA | AGTGAATGAC | TCGACTGTAG | TACAACCTGT |
| 201 | GTCGGATGGA | CCGTATCAAC | CAGCGTCGTT | TGATCTACCA | GTAGGAAATT |
| 251 | GGATGTTGTT | AGCGCCAACA | GGACCAGGTG | TGGTAGTGGA | AGGAACAGAC |
| 301 | AATTCTGGCA | GATGGTTATC | CGAAATTCTA | ATTGAGCCAG | GTGTCACATC |
| 351 | AGAGACAAGA | ACGTATACGA | TGTTTGGATC | AAGTAAACAG | ATGTTAGTGT |
| 401 | CGAACGTGTC | TGATACGAAA | TGGAAATTTG | TTGAAATGAT | GAAGGCGGAG |
| 451 | GTTGATGGTG | ACTATGCGGA | GTGGGGAACA | TTATTATCGG | ACACCAAGCT |
| 501 | CTATGGGATG | ATGAAATATG | GGGAGAGACT | ATTCATATAC | GAAGGAGAAA |
| 551 | CCCCAAATGC | CACGACCAAA | GGATACATCG | TAACGAATTA | TGCATCAGTT |
| 601 | GAGGTAAGGC | CATATAGTGA | CTTTTATATA | ATTTCCAGAT | CACAGGAGTC |
| 651 | GGAGTGCACT | GAATATATAA | ACAACGGGCT | GCCACCCATT | CAAAATACCA |
| 701 | GAAATGTAGT | GCCTGTGGCA | ATATCGTCAA | GATCAATTAA | ACCAAGAGAA |
| 751 | GTCCAAGCTA | ATGAAGATAT | TGTAGTTTCT | AAAACCTCCC | TATGAAAAGA |
| 801 | AATGCAATAT | AATAGAGATA | TCATAATTAG | ATTCAAGTTT | GATAACTCGA |
| 851 | TAATAAAATC | TGGAGGTTTG | GGCTATAAGT | GGGCTGAAAT | CTCATTTAAA |
| 901 | GCTGCAAATT | ATCAATACAA | TTACATAAGA | GACGGAGAAG | AAGTCACAGC |
| 951 | GCATACGACG | TGCTCAGTTA | ATGGTCTTAA | TGATTTTAGC | TTTAACGGAG |
| 1001 | GCTCATTACC | AACGGATTTC | GCAATATCGA | GATATGAAGT | AATTAAAGAA |
| 1051 | AATTCGTATG | TATACGTGGA | CTACTGGGAC | GATTCACAAG | CATCCAGGAA |
| 1101 | TCTGGTCTAC | GTACTATTAT | TAGCAGCGAA | TTTGAATGAC | GTAATGTGTT |
| 1151 | CTGGTGGAGA | TTATAGCTTC | GCTTTACCTG | TTCCACAGTG | GCCAGTGATC |
| 1201 | AAACCAGGGA | CGGTGACGTT | GCACACAGCG | GGAGTAACAT | TATCTACACA |
| 1251 | ATTCACCGAC | TTCGTATCAC | TGAATTCACT | AAGATTTAGG | TTTAGACTGG |
| 1301 | CGGTCGAGGA | ACCCTCATTC | ACGATAACCA | GAACACGTGT | GTCAAAGCCG |
| 1351 | TATGGCCTAC | CAGCAGCCAA | CCCAAACGGC | GGAAAAGAGT | CCTATGAAGT |
| 1401 | GGCTGGAAGG | TTTCCGTTCA | ATTCATTGGT | GCCATCAAAT | GACGATTACC |
| 1451 | CAACGCCAAT | TACGAACTCA | GTAACAGTAA | GGCAAGCATT | GGAAAGGCGC |
| 1501 | TTAAATGAAT | CGAGAGAAGA | ATTCAATAAC | TTGTCACAAG | AGACAGCCGT |
| 1551 | GTCACAGTTA | ATTGACTTAG | CTATGTGGCC | ACTAGACATG | TTTCCGATGT |
| 1601 | TCTCGGAAAT | TGAGAGTACC | GTGATTGCAG | CAAAACCAAT | GGCTACCAAT |
| 1651 | GTGATGAGGA | AGCTTAAGAG | TTCAAAACTC | GCGTCACCAG | TGTCGATGTT |
| 1701 | AAGCGACTCT | TTATCCGATG | CGGCCTACTC | TATCGCAAGA | AGTACACCAG |
| 1751 | TACGATCAAT | AGGACCAACA | GCATCACGTT | GGGCTAATAT | TCCAGAACAG |
| 1801 | ACACAAGACG | CTGTTAGTGA | AGTTGCCACA | ATATCATCAC | AAGTGTCACA |
| 1851 | AATAAGTCCA | AAATTAAGAT | TGAAAGAAAT | TCCGACTCCA | ACAGAGGGAT |
| 1901 | TGAATTTCGA | TGACATATCA | CGGCGGTATT | CAAAAGCCAA | GATAGAAAGA |
| 1951 | TCAATACAGG | TCGCCCCAAA | TGCATTACCA | GACGTCATCA | CAGAAGCGTC |
| 2001 | AGAGAAATTC | ATCCGTAATA | GGGCGTATAG | AGTAATAGAC | GGGGATGAAG |
| 2051 | CATTTGAGGC | GGGCACTGAC | GGAAGATTTT | TCGCGTACAG | GGTGGAAACG |
| 2101 | CTTGAGGAAA | TGCCATTCAA | TATAGAAAAA | TTTGCAGACT | TAGTTACCAA |
| 2151 | CTCACCAGTG | ATATCAGCAA | TAATAGACTT | TAAGACATTG | AAAAACCTGA |
| 2201 | ATGACAATTA | TGGGATAACT | AGAGAGCAAG | CATTTAGTTT | GTTACGGTCA |
| 2251 | GACCCAAAAG | TTTTGCGTGG | ATTTATCGCC | CAAAACAATC | CAATTATAAA |
| 2301 | AAATAGGATA | GAACAGTTGA | TCATGCAATG | TAGATTGTGA | GCAGCTTCTG |
| 2351 | GAGGATGTGA | CC | | | |

Fig. 12

| | | | | | |
|---|---|---|---|---|---|
| 1 | CCATATACAC | CAGATAGTTC | ATTCTTGCCA | TCTAACTATT | GGTATTTAGT |
| 51 | CAATCCATCG | AATGACGGTG | TGGCGTTCTC | AGTAACGGAT | AACAGCACGT |
| 101 | CTTGGATGTT | TACTTATCTA | GCCTTACCAA | ATACAGCTCA | GACTAATGTC |
| 151 | ACAGTAAATG | TGTTGAATGA | GACAGTGAAT | ATATCAATAG | ACAATTCGGG |
| 201 | CTCCACATAT | AGGTTTGTGG | ATTACATTAA | GACTAGCTCC | ACACAAGCGT |
| 251 | ATGGATCGAG | GAACTATCTA | AATACTGCAC | ATAGATTACA | AGCTTACAGA |
| 301 | AGAGATGGAG | ATGGAAATAT | ATCAAATTAT | TGGGGTGCGG | ATACACAAGG |
| 351 | TGACTTAAGG | GTTGGGACAT | ATTCTAATCC | GGTGCCAAAT | GCAGTGATCA |
| 401 | ATCTAAATGC | AGATTTTTAC | GTCATACCAG | ATTCGCAACA | AGAGATATGT |
| 451 | ACAGAATACA | TAAGGGGAGG | ATTGC | | |

Fig. 13

| | | | | | |
|---|---|---|---|---|---|
| 1 | MAWLIYRQLL | DNSYAVDLSD | EIQSVGSEKN | QRVTVNPGPF | AQTGYAPVNW |
| 51 | GPGEVNDSTV | VQPVSDGPYQ | PASFDLPVGN | WMLLAPTGPG | VVVEGTDNSG |
| 101 | RWLSXILIEP | GVTSETRTYT | MFGSSKQMLV | SNYSDTKWKF | VEMMKAEVDG |
| 151 | DYAEWGTLLS | DTKLYGMMKY | GERLFIYEGE | TPNATTNGYI | VTNYASVEVR |
| 201 | PYSDFYIISR | SQESECTEYI | NNGLPPIQNT | RNVVPVAISS | RSIKPREVQA |
| 251 | NEDIVVSKTS | LWKEMQYNRD | IIIRFKFDNS | IIKSGGLGYK | WAEISFKAAN |
| 301 | YQYNYIRDGE | EVTAHTTCSV | NGLNDFSFNG | GSLPTDFAIS | RYEVIKENSY |
| 351 | VYVDYWDDSQ | ASRNLVYVLL | LAANLNDVMC | SGGDYSFALP | VPQWPVIKPG |
| 401 | TVTLHTAGVT | LSTQFTDFVS | LNSLRFRFRL | AVEEPSFTIT | RTRVSKPYGL |
| 451 | PAANPNGGKE | SYEVAGRFPF | NSLVPSNDDY | PTPITNSVTV | RQALERRLNE |
| 501 | SREEFNNLSQ | ETAVSQLIDL | AMWPLDMFPM | FSEIESTVIA | AKPMATNVMR |
| 551 | KLKSSKLASP | VSMLSDSLSD | AAYSIARSTP | VRSIGPTASR | WANIPEQTQD |
| 601 | AVSEVATISS | QVSQISPKLR | LKEIPTPTEG | LNFDDISRRY | SKAKIERSIQ |
| 651 | VAPNALPDVI | TEASEKFIRN | RAYRVIDGDE | AFEAGTDGRF | FAYRVETLEE |
| 701 | MPFNIEKFAD | LVTNSPVISA | IIDFKTLKNL | NDNYGITREQ | AFSLLRSDPK |
| 751 | VLRGFIAQNN | PIIKNRIEQL | IMQCRL | | |

Fig. 14

| | | | | | |
|---|---|---|---|---|---|
| 1 | GTATGGTATT | GAATACCACA | TTCCTAATCT | ACTTGATATC | AATTATATTA |
| 51 | CTTAATTACA | TATTAAAAGT | ATAACTAGAA | TGATGGAGTA | CATAATTTAC |
| 101 | AAATTTTTGC | TTATAGTCAC | AATTACTTCA | ATTGTTGTTA | ATGCACAAAA |
| 151 | TTACGGTATC | AATTTACCAA | TAACCGGATC | AATGGATACA | TCATATGTGA |
| 201 | ATGCACCTAA | AGATGAGCCA | TTTGCTAACG | TCAACATTAT | GTTTTATACT |
| 251 | ATCCAACAGA | AGCTAGAACA | GAGATAAACG | ATAATGAGAG | GACAAGTAGC |
| 301 | GTTGTCAGCA | GCTGTTCTTA | ACAAAGGGAT | CGGCCGACTG | G |

BOVINE ROTAVIRUS GENES

CROSS-REFERENCE TO RELATED APPLICATIONS

This invention is a divisional of the commonly assigned, U.S. patent application Ser. No.: 08/671,978, filed Jun. 28, 1996, now U.S. Pat. No. 5,959,093.

BACKGROUND OF THE INVENTION

Bovine rotavirus (BRV) is a major cause of diarrhea in young calves. Infectious virions of BRV typically have a core protein designated VP2, an inner capsid protein designated VP6, and two outer capsid proteins designated VP4 and VP7. The BRV strains which infect both young and old animals are classified serologically into different groups and subgroups primarily on the basis of epitopes present on VP6. At present there are three BRV groups, designated A, B, and C, which are known to infect calves and adult cattle. The BRV groups are further classified into G serotypes on the basis of epitopes on VP7 and into P serotypes on the basis of epitopes present on VP4. This classification scheme provides important information about the strains of BRV infecting young calves.

Unfortunately, conventional serotyping methods do not permit separate analysis of rotavirus G and P types, and fail to detect subtypes or monotypes of a particular G serotype, limiting their usefulness for field samples.

Recently, a method for genotyping field isolates has been developed which is based on nucleic acid hybridization of probes to viral RNA. The genotyping permits the diagnosis of the strain infecting a particular animal. However the method is limited to diagnosing those strains for which certain genes sequences are known since the production of specific the probes requires knowledge of the gene sequence.

It would be desirable to know the sequences of genes of additional bovine rotavirus strains so as to design probes useful in the diagnosis of bovine rotavirus.

SUMMARY OF THE INVENTION

The present invention relates to novel genes of new field isolates of bovine rotavirus which permit the genotyping and thus the diagnosis of such new strains. The present invention provides the genes encoding the following BRV proteins: for group A, the VP4 and VP7 proteins of the Indiana (IND) strain, and the VP7 protein of the 2292B strain; for group B, the VP7 protein of the WD653 strain; for group C, the VP4 and VP7 proteins of the Shintoku strain. The genes are useful for producing nucleic acid probes which are complementary to the VP7 and VP4 genes. Such probes are useful for detecting the presence of group A,B, and C BRV in fecal samples from diarrheic calves and for determining the serotype of the BRV field isolates. The genes are also useful for producing partial length nucleic acid probes which are complementary to hypervariable regions of the VP4 and VP7 genes.

The present invention also relates to partially purified VP2, VP4, VP6 and VP7 proteins of the IND strain and VP4 and VP7 of the 2292B strain, the partially purified VP7 protein of the WD653 strain, and partially purified VP2, VP4 and VP7 proteins of the Shintoku strain. The present invention also relates to recombinant virus-like particles (VLPs) which comprise one or more of the VP2, VP4, VP6, and VP7 proteins of the BRV strains IND, 2292B, CR, WD653, and Shintoku.

BRIEF DESCRIPTION OF THE FIGURES

FIG. 1 is the nucleotide sequence of the BRV IND VP7 gene (SEQ. ID. NO. 1).

FIG. 2 is the nucleotide sequence of the BRV 2292B VP7 gene (SEQ. ID. NO. 2).

FIG. 3 is the nucleotide sequence of the BRV Shintoku VP7 gene (SEQ. ID. NO. 3).

FIG. 4 is the nucleotide sequence of the BRV WD653 VP7 gene (SEQ. ID. NO. 4).

FIG. 5 is the nucleotide sequence of the BRV Shintoku VP4 gene (SEQ. ID. NO. 5).

FIG. 6 is the deduced amino acid sequence of the BRV IND VP7 protein (SEQ. ID. NO. 6).

FIG. 7 is the deduced amino acid sequence of the BRV 2292B VP7 protein (SEQ. ID. NO. 7).

FIG. 8 is the deduced amino acid sequence of the BRV Shintoku VP7 protein (SEQ. ID. NO. 8).

FIG. 9 is the deduced amino acid sequence of the BRV WD653 VP7 protein (SEQ. ID. NO. 9).

FIG. 10 is the deduced amino acid sequence of the BRV Shintoku VP4 protein (SEQ. ID. NO. 10).

FIG. 11 is the nucleotide sequence of the BRV IND VP4 gene (SEQ. ID. NO. 11).

FIG. 12 is the nucleotide sequence of the BRV Cr VP4 hypervariable region (SEQ. ID. NO. 12).

FIG. 13 is the deduced amino acid sequence of the BRV IND VP4 protein (SEQ. ID. NO. 41).

FIG. 14 is the nucleotide sequence of the BRV Cr VP7 hypervariable region.

DETAILED DESCRIPTION OF THE INVENTION

The genome of group A BRV, group B BRV and group C BRV comprise 11 discrete segments of linear double-stranded RNA, hereinafter referred to as "dsRNA". The dsRNA fragments are numbered 1 to 11 on the basis of their order of migration during polyacrylamide gel electrophoresis. The electrophoretic RNA migration pattern of a BRV strain is referred to as the strain's genomic electropherotype. The genome is enclosed in a triple-layered capsid which is composed of the core viral protein VP2, the inner capsid viral protein VP6, and the outer capsid proteins, VP4 and VP7. The VP4 genotype and VP7 genotype of field isolates enables the design of viral like particles useful as immunogens and vaccines, and which are specifically targeted to the BRV strains that are predominant in the field.

The genes encoding the outer capsid protein VP7 were cloned by PCR amplification from the BRV field strains BRV: Indiana (IND), 2292B, Crocker (Cr), WD653 and Shintoku BRV field strains IND, 2292B, Cr, WD653 and Shintoku were isolated from fecal samples of diarrheic calves/cows in IND, CA, OH, NY and Japan, respectively. The BRV field strains IND, 2292B, CR and Shintoku were serially propagated in monolayers of the fetal rhesus monkey kidney cell line, MA104 cells as described in Tsunemitsu et al., J. Clin. Microb. 29: 2609, 1991 and Saif et al. J. Tissue Culture Methods 11:147–156, 1988. The cell-culture adapted BRV strain IND was deposited with the American Type Culture Collection, 10801 University Boulevard, Manassas, Va. 20110-2209, on Jun. 24, 1996, and has accession number VR-2533. The cell culture adapted BRV strain 2292B was deposited with the American Type Culture Collection on Jun. 24, 1996 and has the Accession Number VR-2534. The cell culture adapted BRV strain Crocker was deposited with the American Type Culture Collection on Jun. 24, 1996 and has accession number VR-2532.

EXAMPLE 1

To prepare genomic dsRNA from the IND strain, the cell-propagated IND strain was subjected to 2 cycles of freezing and thawing, followed by centrifugation at 1,200×g for 30 minutes. The supernatants were centrifuged at 122, 000×g for 3 hours at 4° C. through a 40% sucrose cushion to produce viral pellets. The viral pellets were suspended in 1 ml of extraction buffer which contained 0.1 M sodium acetate, pH 5, and 1% sodium dodecyl sulfate. The suspension was extracted twice with an equal volume of phenol/chloroform mixture (1:1), and 0.1 volume of 4 M sodium acetate and 2 volumes of 100% ethanol were added to the aqueous phase. The RNA was allowed to precipitate overnight at −20° C. and was pelleted by centrifugation at 12,000×g. The RNA was resuspended in diethyl pyrocarbonate (DEP)-treated water and stored at −20° C. until used.

Rotavirus dsRNA in extracted samples was analyzed by polyacrylamide gel electrophoresis to confirm the presence of dsRNA and to examine the genomic electropherotypes. The discontinuous buffer system of Laemmli was utilized, and dsRNA was resolved in 10% polyacrylamide slab gels. Electrophoresis was conducted at 12 mA for 14–16 hours. The dsRNA bands were visualized by silver staining or staining with ethidium bromide having a concentration of 0.5 $\mu$g/ml. The electropherotype of the dsRNA indicated that 11 segments of dsRNA were present and the migration pattern corresponded to that characteristic of the IND strain.

For PCR amplification, the extracted dsRNA was first purified using the RNAid kit from B101, La Jolla, Calif., according to the manufacturer's instructions. Thereafter the purified dsRNA was boiled in 20% dimethyl sulfoxide for 5 minutes and cooled on ice for 5 minutes.

The BRV IND strain VP7 gene was prepared by polymerase chain reaction (PCR) amplification of gene segment 9 using the purified dsRNA as a template and the following sense primer and antisense primer, respectively: 5'CCCGGGATCCATGGCCGGCTTTAAAA GCGAGAATTT 3' SEQ. ID. NO. 19, 5'CGATCGCGAATTCTGCGGCAGGTC, SEQ. ID. NO 20.

Amplification of the dsRNA templates required an initial reverse transcription step. The heat-denatured dsRNA was diluted 1:4 with 5% DMSO in a reaction mixture containing 10 mM Tris (pH 8.3), 40 mM KCl, 1.5 mM $MgCl_2$, 1 mM dithiothreitol, 200 $\mu$M each of dATP, dCTP, dTTP and dGTP, 200 ng each of the sense primer and antisense primer, 10U of AMV reverse transcriptase from Boehinger Mannheim Biochemicals, 2.5 units of Taq polymerase from Boehinger Mannheim Biochemicals and 20 units of RNASIN from Promega.

The tubes were placed in a thermocycler from Perkin Elmer Cetus and incubated at 42° C. to generate cDNA copies of the BRV IND strain dsRNA. The tubes were heated at 94° C. for 5 minutes and subjected to thirty amplification cycles, each consisting of 94° C. for 1 minute to denature the cDNA, 42° C. for 1.5 minutes to anneal the primer to the nucleic acid and 72° C. for 3.5 minutes to extend the strands. The PCR products were purified and analyzed by 1% agarose gel using standard techniques. The PCR products were cloned into the pCRII plasmid from Invitrogen according to manufacturer's instructions and sequenced using the primer extension method of Sambrook et al. (1989) Molecular Cloning: a Laboratory Manual, Cold Spring Harbor Laboratory Press, Cold Spring Harbor, N.Y.

As shown in FIG. 1, the VP7 gene of IND strain, SEQ. ID. NO. 1, comprises 1062 base pairs. An AUG codon at base 49 initiates a 978 base pair open reading frame and codes for 326 amino acids. The deduced amino acid sequence of the VP7 protein of the IND strain, SEQ. ID. NO. 6 is shown in FIG. 6.

EXAMPLE 2

Genomic dsRNA was extracted from the cell-propagated 2992 B strain as described in Example 1 and the extracted dsRNA purified as described in Example 1. The BRV 2292B strain VP7 gene was prepared by PCR amplification of gene segment 9 from the 2292 strain dsRNA template using the following sense primer and antisense primer, respectively

5'CCCGGGATCCATGGCCGGCTTTAAAA GCGAGAATTT 3' SEQ. ID. NO. 19

5'CGATCGCGAATTCTGCGGCAGGTC, SEQ. ID. NO 20.

Amplification of the template was conducted as described in Example 1. The sequence of the VP7 gene of the 2992B strain, SEQ. ID. NO. 2, is shown in FIG. 2. The deduced amino acid sequence of the VP7 protein of the 2992, SEQ. ID. NO. 7, strain is shown in FIG. 7.

EXAMPLE 3

Genomic dsRNA was extracted from the cell-propagated Shintoku strain as described in Example 1 and the extracted dsRNA purified as described in Example 1. The BRV Shintoku strain VP7 gene was prepared by PCR amplification of gene segment 8 from the Shintoku strain dsRNA template using the following sense primer and antisense primer, respectively:

5'-GGCATTTAAAAAAGAAGAAGCTGT-3', SEQ. ID. NO. 27

5'-AGCCACATGATCTTGTTTACGC-3', SEQ. ID. NO. 28.

The dsRNA template was added to a reaction mixture as described in Example 1. The mixture was overlaid with mineral oil and then subjected to one cycle of reverse transcription at 42° C. for 30 minutes and 30 cycles of PCR amplification at 94° C. for 1 minute, 42° C. for minutes. and 72° C. for 3 minutes and a final 7 minute incubation at 72° C. The PCR products were sequenced using the Sequenase version 2 DNA sequencing kit from United States Biochemical. Single-stranded sequencing templates were prepared by digestion of the phosphorylated strand of the PCR products with lambda exonuclease from Pharmacia Biotech. Sequences of both terminal regions of the VP7 genes were determined by a modified procedure of Lambden et al. J. Virol. 66: 1817–1822, 1992. Synthetic primer 1, 5'CCCGTCGACGAATTCTTT-3'-$NH_2$, SEQ.ID.NO. 46 was ligated to the 3' ends of the viral RNA using T4 RNA ligase from GIBCO/BRL. cDNA fragments of 400 to 600 base pairs spanning either the 5' or the 3' ends were produced by RT-PCR using primer 2 complementary to primer 1 and virus-specific primers, and were sequenced by using internal primers. The sequence of the VP7 gene of the Shintoku strain, SEQ. ID. NO. 3, is shown in FIG. 3. The deduced amino acid sequence of the VP7 protein of the Shintoku strain, SEQ. ID NO. 8, is shown in FIG. 8.

The VP7 gene of the Shintoku strain comprises 1063 nucleotides and contains one open-reading-frame encoding a polypeptide of 332 amino acids. The predicted molecular mass of the VP7 gene from the group C Shintoku BRV is 37.3 to 37.6 kDa.

EXAMPLE 4

Genomic dsRNA was extracted from the cell-propagated WD653 strain as described in Example 1 and the extracted dsRNA purified as described in Example 1. The BRV WD653 strain VP7 gene was prepared by PCR amplification of the corresponding gene segment 9 from the 2292 strain dsRNA template using the following sense primer and antisense primer, respectively

5'GGAAATATCAGAGATGCGT 3' SEQ. ID. NO. 21.

5'TTCTTTATGCTTCGGCCTA 3' SEQ. ID. NO. 22.

Amplification of the template was conducted as described in Example 1. The sequence of the VP7 gene of the WD653 strain, SEQ. ID. NO. 4, is shown in FIG. 4. The deduced amino acid sequence of the VP7 protein of the WD653 strain, SEQ. ID. NO. 9, is shown in FIG. 9.

EXAMPLE 5

Genomic dsRNA was extracted from the cell-propagated Shintoku strain as described in Example 1 and the extracted dsRNA purified as described in Example 1. The BRV Shintoku strain VP4 gene was prepared by PCR amplification of gene segment 4 from the Shintoku strain dsRNA template using the following sense primer and antisense primer, respectively

5'GGAAATATCAGAGATGCGT 3' SEQ. ID. NO.23

5'TTCTTTATGCTTCGGCCTA 3' SEQ. ID. NO.24.

Amplification of the template was conducted as described in Example 1. The sequence of the VP4 gene of the Shintoku strain, SEQ. ID. NO. 5, is shown in FIG. 5. The deduced amino acid sequence of the VP4 protein of the IND strain, SEQ. ID. NO. 10, is shown in FIG. 10.

EXAMPLE 6

Genomic dsRNA was extracted from the cell-propagated IND strain as described in Example 1 and the extracted dsRNA purified as described in Example 1. The BRV IND strain VP4 gene was prepared by PCR amplification of gene segment 4 from the IND strain dsRNA template using the following sense primer and antisense primer, respectively

5'CCCGGGATCCGAATTCGGCTATAAAATGGCTTGGCT 3' SEQ. ID. NO. 15

5'TCGCGAATTCTGCAGGTACATCCTCCAGAAGCT 3' SEQ. ID. NO. 16.

Amplification of the template was conducted as described in Example 1. The sequence of the VP4 gene of the IND strain, SEQ. ID. NO. 11, is shown in FIG. 11. The deduced amino acid sequence of the VP4 protein of the IND strain, SEQ. ID. NO. 13, is shown in FIG. 13.

EXAMPLE 7

Genomic dsRNA was extracted from the cell-propagated Cr strain as described in Example 1 and the extracted dsRNA purified as described in Example 1. The BRV Cr strain VP4 gene was prepared by PCR amplification of corresponding gene segment from the Shintoku strain dsRNA template using the following sense primer and antisense primer, respectively

5'CCCGGGATCCGAATTCGGCTATAAAATGGCTTGGCT 3' SEQ. ID. NO. 15

5'TCGCGAATTCTGCAGGTACATCCTCCAGAAGCT 3' SEQ. ID. NO. 16.

Amplification of the template was conducted as described in Example 1. The sequence of the hypervariable region of the VP4 gene of the Cr strain, SEQ. ID. NO. 12 is shown in FIG. 12.

Diagnosing Infection with BRV cDNA probes, preferably full-length cDNA probes, complementary to the VP4 or VP7-encoding gene segments isolated from BRV strains IND, 2292B, and Cr, are useful for diagnosing infection with group A virus in fecal samples from diarrheic animals. cDNA probes, preferably full-length cDNA probes, complementary to the VP7-encoding gene segment isolated from WD653 strain, are useful for diagnosing infection with Group B rotaviruses, and cDNA probes, preferably full-length cDNA probes, complementary to the VP4 and VP7 encoding gene segments from the Shintoku strain are useful for diagnosing infection with group C rotaviruses. The cDNA probes are prepared by PCR amplification of dsRNA extracted from the virus strains using primers for the 5' ends of the sense and antisense strands. The preferred primers for preparing the full-length cDNA probes of the VP4 and or VP7 genes of BRV strains IND, 2292B, Cr, WD653 and Shintoku, are shown in Table 1.

TABLE 1

Oligonucleotide primers for PCR Amplification of full-length cDNAs.

| Genes | Primer | Sequences | |
|---|---|---|---|
| IND,2922B,Cr (Group A) | | | |
| VP2 | Sense | 5'GGCTATTAAAGGT 3' | SEQ. ID. NO. 13 |
| | Antisense | 5'GGTCATATCTCCACA 3' | SEQ. ID. NO. 14 |
| VP4 | Sense | 5'CCCGGGATCCGAATTCGGCTATAAA ATGGCTTGGCT 3' | SEQ. ID. NO. 15 |
| | Antisense | 5'TCGCGAATTCTGCAGGTACATC CTCCAGAAGCT 3' | SEQ. ID. NO. 16 |
| VP6 | Sense | 5'GGCTTTTAAACGAAGTC 3' | SEQ. ID. NO. 17 |
| | Antisense | 5'GGTCACATCCTCTCACTA 3' | SEQ. ID. NO. 18 |
| VP7 | Sense | 5'CCCGGGATCCATGGCCGGCTTTAAAA GCGAGAATTT 3' | SEQ. ID. NO. 19 |
| | Antisense | | |

TABLE 1-continued

Oligonucleotide primers for PCR Amplification of full-length cDNAs.

| Genes | Primer | Sequences | |
|---|---|---|---|
| | | 5'CGATCGCGAATTCTGCGGCAGGTC | SEQ. ID. NO. 20 |
| WD563 (Group B) | | | |
| VP7 | Sense | 5'GGAAATATCAGAGATGCGT 3' | SEQ. ID. NO. 21 |
| | Antisense | 5'TTCTTTATGCTTCGGCCTA 3' | SEQ. ID. NO. 22 |
| Shintoku (Group C) | | | |
| VP4 | Sense | 5'GGAAATATCAGAGATGCGT 3' | SEQ. ID. NO. 23 |
| | Antisense | 5'TTCTTTATGCTTCGGCCTA 3' | SEQ. ID. NO. 24 |
| VP6 | Sense | 5'GCATTTAAAATCTCATTCAC 3' | SEQ. ID. NO. 25 |
| | Antisense | 5'AGCCACATAGTTCACATTTC 3' | SEQ. ID. NO. 26 |
| VP7 | Sense | 5'GCATTTAAAAAAGAAGAAGCTGT 3' | SEQ. ID. NO. 27 |
| | Antisense | 5'AGCCACATGATCTTGTTTACGC 3' | SEQ. ID. NO. 28 |

The cDNA probes are used in hybridization assays with total RNA extracted with phenol/chloroform from fecal samples of calves suspected of having a BRV infection. Preferably, the hybridizations are performed under conditions of moderate stringency, for example, for 16–24 hours at 42° C., when the full length probes are used to detect the presence of Group A, B, and C BRV.

Typing BRV Infections

Probes that are complementary to the hypervariable region of the VP4 and VP7 genes are useful for characterizing the specific genotype of the BRV strain in field isolates. The hypervariable region sequence also serves as the basis for genotyping either G or P type field isolates by a method which employs reverse transcription PCR (RT-PCR) amplification of the hypervariable region and analysis of the size of the PCR product.

The P type and G type of BRV obtained from field isolates are assayed by hybridizing cDNA probes which are complementary to hypervariable regions of the VP4 and VP7 genes of different BRV strains to the dsRNA isolated from fecal samples of diarrheic animals.

The partial-length VP4 and VP7 cDNA probes used in the assays are made by PCR amplification, such as using the techniques described in Examples 1–7 of the cloned genes using primers having sequences complementary to the highly conserved regions of the VP4 and VP7 genes and which flank the hypervariable regions of the VP4 and VP7 genes. Examples of suitable primers for PCR amplification of the hypervariable regions of the VP4 and VP7 genes of BRV strains IND, Cr, 2992B, Shintoku are shown in Table 2. Alternatively, the partial length VP4 and VP7 probes are made using nucleic acid synthesizers. The purified PCR products are then radiolabeled, preferably by using a nick translation kit, such as the kits available from Bethesda Research Laboratories, Gaithersburg, Md.

The dsRNA is extracted from fecal samples obtained from the BRV infected cow or calf with phenol/chloroform as described in Parwani, et al., *J. Clinical Microbiology*, August 1993, Vol. 31, No. 8, pp. 2010–2015. The dsRNA isolate is then resolved by polyacrylamide gel electrophoresis and denatured by soaking the gel in 0.1 M NaOH and 0.25 M NaCl for 20 minutes at room temperature. The gel is then washed, preferably twice for 20 minutes each time in 4×TAE (I×TAE=0.01 M Tris-acetate, 0.001 M ethylenediaminetetraacetic acid) and once in 1×TAE for 20 minutes. The denatured RNA is electrotransferred, preferably onto Nytran membranes and immobilized using ultraviolet light cross-linking.

For dot blots, dsRNA is preferably denatured at 95° C. for 5 minutes and placed on ice for 5 minutes. The RNA is preferably dotted onto nylon membranes in volumes of 5 $\mu$l or less. Following application of the samples, the membranes are air dried and baked for 2 hours at 80° C. in a vacuum oven.

The membranes are prehybridized for preferably 4 hours at 42° C. or 52° C. in hybridization buffer containing 50% formamide, 5×standard saline citrate, 50 mM phosphate buffer at pH 6.5, 0.2% SDS, 2×Denhardt's solution, 100 $\mu$g/ml yeast tRNA. Hybridization is performed preferably in 3–5 ml of hybridization buffer containing 4.5% dextran sulfate and 3–5x$10^6$ counts/minute of heat-denatured PCR probe of approximately 1.2x$10^7$ CPM/$\mu$gDNA template. Preferably, the hybridizations are performed under condition of high stringency, for example, for 16–24 hours at 52° C., when the partial probes are used to genotype the field isolates. The membranes are washed 4 times at room temperature in 2×SSC and 0.1% SDS and 2 times at hybridization temperature in 0.4×SSC and 0.1% SDS. The washed membranes are rinsed once with water, blotted, and exposed to film with intensifying screens at −70° C.

Alternatively, the genotypes of field isolates are determined as in the methods described in Examples 1–7 by isolating dsRNA from the field isolate, preparing cDNA molecules by RT-PCR employing the sense and antisense primers shown in Table 2, cloning the cDNA into a vector, sequencing the cDNA and comparing the sequence obtained to the disclosed sequences for the VP4 and VP7 genes of BRV strains IND, 2292B, Cr, WD653 and Shintoku.

TABLE 2

Sequences of oligonucleotides used for PCR-amplification of partial length VP4 and VP7 genes

| Gene | Location | Strand[3] | Sequence | |
|---|---|---|---|---|
| VP4 (IND, 2292B, Cr) | Nucleotides 211 to 230 | Sense | 5'-CCGTATCAGCCGGCGCCGTT-3'- | SEQ.ID.NO. 29 |
| VP4 (IND, 2292B, Cr) | Nuclcotides 677 to 686 | Anti-sense | 5'-GGCGGCAGCCCGTTGTTTAT-3'- | SEQ.ID.NO. 30 |
| VP7 (IND, 2292B, Cr) | Nuclcotides 51 to 71 | Sense | 5'-GTATGGTATTGAATATACCAC-3'- | SEQ.ID.NO. 31 |
| VP7 (IND, 2292B, Cr) | Nucleotides 376 to 392 | Anti-sense | 5'-GATCCTGTTGGCCATCC-3'- | SEQ.ID.NO. 32 |
| VP4 (Shintoku) | Nucleotides 1–20 | Sense | 5'-GGCTTAAAAAAGTCAGGATC-3'- | SEQ.ID.NO. 33 |
| VP4 (Shintoku) | Nucleotides 408–425 | Anti-sense | 5'-TCAGAATTTGTCATCCCT-3'- | SEQ.ID.NO. 34 |
| VP4 (Shintoku) | Nucleotides 640–647 | Anti-sense | 5'-AATGTTCATGCTCGCACT-3'- | SEQ.ID.NO. 35 |
| VP4 (Shintoku) | Nucleotides 1768–1785 | Sense | 5'-CCAAGAAGTACTACCGC-3'- | SEQ.ID.NO. 36 |
| VP4 (Shintoku) | Nucleotides 1967–1984 | Sense | 5'-CTTATGATTTGGCTACTC-3'- | SEQ.ID.NO. 37 |
| VP4 (Shintoku) | Nucleotides 2234–2253 | Anti-sense | 5'-AGCCACATAATAAGTCGATC-3'- | SEQ.ID.NO. 38 |
| VP7 (Shintoku) | Nucleotides 1-20 | Sense | 5'-GGCATTTAAAAAAGAAGAAG-3'- | SEQ.ID.NO. 39 |
| VP7 (Shintoku) | Nucleotides 145–163 | Anti-sense | 5'-CAAAAGCAATAAGTGACAA-3'- | SEQ.ID.NO. 40 |
| VP7 (Shintoku) | Nucleotides 302–319 | Anti-sense | 5'-GACCAGGTCGCCCCACTG-3' | SEQ.ID.NO. 42 |
| VP7 (Sttintoku) | Nucleotides 411–429 | Anti-sense | 5'-AGTATAAGTATTAAAATTC-3' | SEQ.ID.NO. 43 |
| VP7 (Shitoku) | Nucleotides 844–861 | Sense | 5'-GTAAGAATTTCGAACTTG-3'- | SEQ.ID.NO. 44 |
| VP7 (Shintoku) | Nucleotides 1044–1063 | Anti-sense | 5'-AGCCACATGATCTtGTTTAC-3'- | SEQ.ID.NO. 45 |

Expression of the VP4 and VP7 Genes

Partially-purified BRV proteins VP2, VP4, VP6 and VP7 are obtained from the IND strain, the 2292 B strain, the WD563 strain and the Shintoku strain by extracting the dsRNA of each strain from cell-culture lysates or infected gnotobiotic calf fecal material, preparing amplified cDNA from the dsRNA by reverse-transcription (RT) PCR using gene specific primers for the 5' and 3' ends of the sense and antisense strand of the dsRNA, constructing a recombinant vector with the amplified DNA, transfecting cells with the recombinant vector, lysing the cells, and centrifuging the cell lysates to provide a supernatant containing the partially purified protein. Further purification is accomplished by affinity chromatography using viral protein specific monoclonal antibodies to purify the corresponding protein. The preferred gene specific primers for RT-PCR of the genes which encode the viral proteins from the IND strain, the 2992B strain, the Cr strain, the WD563 strain and the Shintoku strain are shown in Table 1.

EXAMPLE 8

The partially-purified VP4 protein of the IND strain was prepared by first amplifying genomic dsRNA extracted from the cell-propagated IND strain as described in Example 1 using a sense primer of SEQ. ID. NO. 15 and the antisense primer SEQ. ID. NO. 16 as shown in Table 1. The PCR-amplified full length VP7 cDNA was purified by centrifugation using a centrix-AG cartridge from Advanced Genetic Technologies, Gaithersburg, and then digested with restriction enzymes BamHI and PstI. The VP4 fragments were then cloned into plasmid pVL1393 from Pharmigen, San Diego. Recombinant plasmids were identified by colony blot hybridization using radiolabeled PCR-derived IND VP4 cDNA as a probe. The probes were prepared using a nick translation kit from Bethesda Research Laboratories, Gaithersburg and $^{32}$P-deoxycytidine-5'-triphosphate from ICN Biochemicals, Irvine, Calif. Plasmid DNAs hybridizing positively with the probes were subjected to restriction enzyme digests to check the size of the inserts. The recombinant plasmids were identified by sequencing in the junction region toward 3' and 5' end of the IND VP4 cDNA using polyhedron forward primer 5'-AAATGATAACCATCTCGA-3', SEQ. ID NO. 49 or the reverse primer 5'-GTCCAAGTTTCCCTG-3', SEQ. ID. NO. 50.

A cationic liposome mediated transfection kit from Invitrogen, San Diego was used to transfect the recombinant baculovirus into Sf9 cells. Sf9 cells were seeded in 60 mm plates and transfected with a mixture of 3 $\mu$g of recombinant transfer plasmid, 1 $\mu$g of linear AcMNPV viral DNA and 20 $\mu$l of cationic liposome solution. The transfected cells were incubated at 27° C. for 4 to 5 days. Successful transfection was confirmed by the presence of polyhedron within 6 days of transfection.

Serial dilution of the cell culture supernatants obtained from transfected Sf9 cells were used for a plaque assay. Recombinants were selected by occlusion-negative plaques. Virus in occlusion-negative plaques was subjected to three rounds of plaque purifications and used to propagate virus stock.

To confirm the recombination, the cell lysates from mock or recombinant baculovirus infected Sf9 cell monolayers was harvested and total DNA was purified by PEG/NaCl method. The presence of recombinants in the total DNA purified from infected Sf9 cells was determined by PCR using the following primers: 5'-TTTACTGTTTTCGTAACAGTTTTG-3', SEQ. ID. NO. 47, and 5'-CAACAACGCACAGAATCTAGC-3', SEQ. ID. NO. 48. The PCR reactions were heated at 94° C. for 2 minutes and subjected to thirty amplification cycles, each consisting of 94° C. for 1 minute, 55° C. for 2 minutes, 72° C. for 3 minutes and one cycle at 72° C. for 7 minutes. The PCR products were purified by centrix-AG cartridge from Advanced Genetic Technologies, Gaithersburg, Md., and analyzed by 1% agarose gel electrophoresis.

An indirect immunofluorescence assay was used to detect the expression of the IND VP7 protein in the infected Sf9 cells. Confluent Sf9 cells grown in 24-well plates were mock infected or infected with recombinant baculoviruses and incubated at 27° C. for 2 to 3 days. After the end of the incubation, the cells were harvested, centrifuged and washed with phosphate buffered saline. The cells were placed on 8 well slides, air dried and fixed with 80% acetone. Guinea pig hyperimmune antiserum to IND BRV was used to detect the expressed proteins. Antiserum at a dilution of 1:500 was incubated with the infected cells at 37° C. for 1 hr. The slides were placed in PBS for 5 minutes. The cells were then incubated with fluorescein-labeled rabbit anti guinea pig serum at a 1:1,000 dilution at 37° C. for 1 hour. Following this, the cells were washed and examined using a fluorescence microscope.

Cells which exhibited a positive fluorescence were sonicated at 40 amplitude for 1 minute, centrifuged at 2000 RPM for ten minutes at 4° C., and the supernatants collected from to provide the partially-purified VP7 protein of the IND strain. Each ml of cell lysate supernatant contained the partially purified VP7 protein from $10^7$ transfected cells.

EXAMPLE 9

The partially-purified VP7 of the IND strain was prepared first by PCR amplifying the dsRNA extracted from the cell-propagated IND strain as described in Example 1 using the sense primer having SEQ. ID. NO. 19 and the antisense primer SEQ. ID. NO. 20 as shown in Table 1. The PCR-amplified full length VP4 cDNA was purified as described in Example 8 and then digested with restriction enzymes EcoRI and BamHI and cloned into plasmid pVL1393 from Pharmigen, San Diego. Recombinant plasmids were identified as described in Example 8 and used to transfect Sf9 cells as described in Example 8. Transfected cells were identified as described in Example 8, and×106 transfected cells were sonicated, and centrifuged to provide a supernatant containing partially purified VP4 protein of the IND strain. Each ml of cell lysate supernatant contained the partially purified VP7 protein from $10^7$ transfected cells.

EXAMPLE 10

The partially-purified VP7 of the Shintoku strain was prepared first by PCR amplifying dsRNA from the cell-propagated Shintoku strain as described in Example 1 using the sense primer having SEQ. ID. NO. 25 and the antisense primer SEQ. ID. NO. 26 as shown in Table 1. The PCR-amplified full length VP7 cDNA was purified as described in Example 4 and then digested with restriction enzymes EcoRI and BamHI and cloned into plasmid pCR-Bac from Invitrogen, San Diego. Recombinant plasmids were identified by DNA sequencing in the junction region toward the 3' and 5' end of each gene using polyhedron forward primer 5'-AAATGATAACCATCTCGC-3', SEQ.ID.NO. 49 or the reverse primer, 5'-GTCCAAGTTTCCCTG-3, SEQ. ID. NO. 50.

Recombinant plasmids were used to transfect Sf9 cells as described in Example 4. Transfected cells were identified as described in Example 8, sonicated, and centrifuged to provide a supernatant containing partially purified VP7 protein of the Shintoku strain. Each ml of cell lysate supernatant contained the partially purified VP7 protein from $10^7$ transfected cells.

EXAMPLE 11

The partially-purified VP4 of the Shintoku strain was prepared first by PCR amplification of the dsRNA obtained from the cell-propagated Shintoku strain as described in Example 1 using the sense primer having SEQ. ID. NO. 23 and the antisense primer SEQ. ID. NO. 24 as shown in Table 1. The PCR-amplified full length VP4 cDNA was purified as described in Example 8 and then digested with restriction enzymes EcoRl and BamHI and cloned into plasmid pCR-Bac from Invitrogen, San Diego. Recombinant plasmids were identified as described in Example 10 and used to transfect Sf9 cells as described in Example 8. Transfected cells were identified as described in Example 8. The supernatant containing partially purified VP4 protein of the Shintoku strain was prepared as in Example 8. Each ml of cell lysate supernatant contained the partially purified VP7 protein from $10^7$ transfected cells.

EXAMPLE 12

The partially-purified VP6 protein of the Shintoku strains was prepared first by PCR amplification of the dsRNA from the cell-propagated Shintoku strain and PCR as described in Example 1 using the sense primer having SEQ. ID. NO. 25 and the antisense primer SEQ. ID. NO. 26 as shown in Table 1. The PCR-amplified full length VP6 cDNA was purified as described in Example 4 and then digested with restriction enzymes EcoRI and BamHI and cloned into plasmid pCR-Bac from Invitrogen, San Diego. Recombinant plasmids were identified as described in Example 6 and used to transfect Sf9 cells as described in Example 4. Transfected cells were identified as described in Example 4, sonicated, and centrifuged to provide a supernatant containing partially purified VP6 protein of the Shintoku strain. Each ml of cell lysate supernatant contained the partially purified VP7 protein from $10^7$ transfected cells.

EXAMPLE 13

The partially-purified VP6 protein of the IND strain was prepared first by PCR amplification of the dsRNA from the cell-propagated IND strain as described in Example 1 using the sense primer having SEQ. ID. NO. 17 and the antisense primer SEQ. ID. NO. 18 as shown in Table 3. The PCR-amplified full length IND VP6 cDNA was purified as described in Example 4 and then digested with restriction enzymes EcoRi and BamHI cloned into plasmid pCR-Bac. Recombinant plasmids were identified as described in Example 6 and used to transfect Sf9 cells as described in Example 4. Transfected cells were identified as described in Example 4. Transfected cells were sonicated, and centrifuged to provide a cell lysate supernatant containing partially purified VP6 protein of the IND strain. Each ml of cell lysate supernatant contained the partially purified VP6 protein from $10^7$ transfected cells.

Immunization of Animals with Partially Purified VP4, VP6, and VP7 Proteins from Recombinant Baculovirus Cell Lysates The partially-purified IND VP4 protein, IND VP7 protein, Shintoku VP4 protein and Shintoku VP7 protein respectively of Examples 8, 8, 10, and 11 were injected into guinea pigs. 0.5 ml of the cell lysate supernatant containing the respective partially-purified viral protein was mixed with an equal volume of Freund's complete adjuvant and the entire amount injected into multiple subcutaneous sites of each animal. Two weeks later, booster injections of the same amount of cell lysate supernatant mixed with an equal volume of Freund's incomplete adjuvant were administered. The same inoculum with adjuvant was administered intramuscularly at three-week intervals after the second injection up to 4 times. The guinea pigs were bled at 3 and 7 weeks via cardiac puncture after the first injection. Serum samples were tested for the presence of virus neutralizing antibodies by plaque reduction virus neutralization (PRVN) assays and for the presence of antibodies reactive to rotavirus by ELISA, western blot and immunofluorescence assays.

The PRVN test was performed in six well plates containing MA 104 cell monolayers to determine neutralizing antibody titers of the hyperimmune antisera to the recombinant proteins. Serial four fold dilutions of antisera were mixed with equal volumes of viral suspensions containing 60 to 80 PFU/0.1 ml and incubated for one hour at 37° C. The plates were washed once with serum free Earle's Minimal Essential Medium and agar medium containing 0.8% Noble agar, 0.067 mg of neutral red per ml, and 25 $\mu$g of pancreatin from Gibco per ml in E-MEM was added. The PRVN titer was expressed as the reciprocal of the highest dilution of serum which produced an 80% reduction in the number of plaques, as compared with the number in virus control wells. The PVRN titers for animals mock-infected baculovirus lysates and with the partially purified proteins of Examples 4, 5, 6, and 7 are shown in Table 4.

TABLE 4

PRVN titers of Animals injected with Partially-Purified VP4 and VP7 Proteins of the IND and Shintoku BRV strains

| Sample (No. of Immunizations) | Volume Injected | PRVN Titer |
|---|---|---|
| Mock Sf9 cells | 1 ml | <4 |
| Mock Sf (2) | 2 ml | <4 |
| IND VP4 | 1 ml | <64 |
| IND VP4 (2) | 1 ml | |
| IND VP4 (5) | 5 ml | 610 |
| IND VP4 (2) | 1 ml | <64 |
| IND VP4 (5) | 5 ml | 150 |
| IND VP7 (1) | 1 ml | <4 |
| IND VP7 (2) | 2 ml | <4 |
| IND VP7 (5) | 0.5 ml | <64 |
| Shintoku VP7 (1) | 1 ml | <4 |
| Shintoku VP7 (4) | 1 ml | <4 |
| Shintoku VP4 (4) | 1 ml | 150 |

Characterizing the Antibody Titer of Animals

The partially-purified VP4 and VP7 proteins of the BRV strains IND, 2992B, Cr, WD653 and Shintoku are useful for measuring the titers of VP4 and VP7 antibodies in serum samples of animals naturally infected with BRV strains having serogroups or serotypes related to each of these respective BRV strains or in animals inoculated with a vaccine made with the related whole virus. The method of measurement involves a direct ELISA testing system using the partially-purified proteins coated directly on the plates or captured on the plates via antibodies.

EXAMPLE 14

Nunc plates are coated directly with the supernatant of Examples 4, 5, 6, and 7 diluted 1:25 or with lysates of wild-type baculovirus-infected cells control diluted 1:25. Serum samples from the animals inoculated with the test vaccine are added to each plate. Then secondary antibodies consisting of biotinylated monoclonal antibodies to bovine IgGI; IgG2; and IgM diluted 1:1,000–1:2,000 are added to the plate. The indicator antibody is a peroxidase-conjugated streptavidin$^b$ diluted 1:10,000 and the substrate is 2,2 acino-di-(e-ethylbenz-thiazoline-6-sulfonate) with 0.03% $H_2O_2$. For detection of IgA antibodies in the above system, a monoclonal antibody conjugated to alkaline phosphatase diluted 1:500 is used followed by the substrate p-nitrophenol phosphate in 10% DEA buffer. The absorbance for all assays, is determined in an ELISA reader at 405 nm for the alkaline phosphatase system or 450 nm for the peroxidase system. The ELISA antibody titers are expressed as the reciprocal of the highest sample dilution which had an absorbance of greater than 3 SD above the background control sample in mock-infected wild type control wells. Each test includes a positive and negative control serum.

Preparation of Virus-Like Particles

It is currently believed that vaccines which elicit a strong immunogenic response to the outer capsid proteins VP4 and VP7 offer greater protection than vaccines which elicit only a weak immunogenic response to these outer capsid proteins. Unfortunately, vaccines made from live and attenuated viruses do not always raise a high antibody titer to VP4 and VP7. The viruses that are used in such vaccines are obtained from tissue culture and are not always complete, that is, the tissue culture-propagated viruses lack the outer capsid layer. Moreover, the compounds which are used to inactivate the viruses used in vaccines are believed to adversely affect the epitopes which elicit a strong immune response. Accordingly, it is desirable to have a non-infectious, immunogenic virus particle which is comprised of the viral triple capsid layers and the VP2, VP4, VP6 and VP7 proteins. It is also desirable to have a method of assessing the VP4 and VP7 antigenicity of vaccines made with attenuated or inactivated viruses or with immunogenic virus-like particles.

Rotavirus virus-like particles (VLPs) are assembled in a triple-layered structure by coinfecting cells with four different recombinant vectors, wherein one of said vectors comprises a rotavirus VP2 gene, one of said vectors comprises a rotaviarus VP4 gene, one of said vectors comprises a rotavirus VP6 gene, and one of said vectors comprises a rotavirus VP7 gene, and then isolating the assembled particles from the extracellular medium or cell lysates. Preferably the cells are infected with the recombinant vector at a multiplicity of infection of from about 5 to about 10 plaque-forming units (PFUs). Preferably the VLP comprises at least one BRV protein. To form homologous VLP's, the cells are coinfected with vectors that comprise genes from the same BRV strain. Preferably, the vectors used to prepare a homologous VLP comprise the VP2, VP4, VP6, and VP7 genes from one of the following BRV strains: the IND strain, the 2292B strain, the Shintoku strain, the Cr strain, or the WD653 strain. To form heterologous VLPs, the cells are coinfected with vectors that comprise the VP2, VP4, VP6, and VP7 genes from different strains of rotavirus. For heterologous VLPs, it is preferred that the cells be coinfected with baculoviruses comprising the VP4 and VP7 genes from a single BRV strain, more preferably the IND strain, the 2292B strain, the Shintoku strain, or the WD653 strain.

EXAMPLE 15

A heterologous VLP was prepared by coinfecting Sf9 cells at a multiplicity of infection of 10 PFU per cell with baculovirus recombinants which comprised of genes encoding the core BRV proteins RF VP2, SA11 VP6, and the outer capsid proteins IND VP4, and IND VP7. The baculovirus recombinants comprising the IND VP4 protein and the IND VP7 protein were prepared as described in Examples 8 and 9, respectively. The baculovirus recombinants were prepared using rotavirus genes 2 and 6 obtained from Dr. M. K. Estes, Baylor College of Medicine, Houston, Tex. The infection was done in Hink's TNM-FH insect medium from JRH, Lenexa, Kans., containing 0.5% FBS. The cells and medium were harvested at 144 hours postinfection, and the medium was clarified by centrifugation for 10 minutes at 2,500 rpm in a Hermle centrifuge. The clarified medium was layered over a 35% sucrose cushion in TNC buffer and centrifuged for 90 minutes at 25,000 rpm in a Beckman SW28 rotor. The resulting pellet was suspended in TNC buffer containing 10 mM Tris-Cl, 140 mM NaCl, 10 mM $CaCl_2$. Cesium chloride was added to the pellet to obtain a refractive index of 1.3640, and the mixture was centrifuged for 18 hours at 35,000 rpm in a Beckman SW50.1 rotor. The resulting cesium chloride gradients were fractionated, and fractions which contained the triple-layered VLPs were pooled. The VLPs were then concentrated by centrifugation for 2 hours at 35,000 rpm in a Beckman SW41 rotor, the supernatant removed, and the VLP pellet suspended in TNC buffer. Particle composition and integrity was determined by negative-stain electron microscopy (EM), Western blot, and ELISA.

Administering the VLP p 0.5 ml of the VLP suspension of Example 10 was mixed with an equal volume of Freund's complete adjuvant and the entire amount injected into the multiple subcutaneous sites in each guinea pig. Two weeks later, booster injections of the same amount of suspension with an equal volume of Freund's incomplete adjuvant were administered. The same inoculum with adjuvant was administered intramusculary at three-week intervals after the second injection up to 4 times. The guinea pigs were bled at 3 and 7 weeks via cardiac puncture after the first injection. Serum samples were tested for the presence of virus neutralizing antibodies by PRVN assays and for the presence of antibodies to rotavirus by ELISA, western blot and immunofluorescence assays.

The PRVN test was performed in six well plates containing MA 104 cell monolayers to determine neutralizing antibody titers of the hyperimmune antisera to the VLP particles. Serial four fold dilutions of antisera were mixed with equal volumes of viral suspensions containing 60 to 80 PFU/0.1 ml and incubated for one hour at 37° C. The plates were washed once with serum free Earle's Minimum Essential Medium, and agar medium containing 0.8% Noble agar, 0.067 mg of neutral red per ml, and 25 μl of pancreatin from Gibco per ml in E-MEM was added. The PRVN titer was expressed as the reciprocal of the highest dilution of serum which produced an 80% reduction in the number of plaques, as compared with the number in virus control wells.

The PVRN titers for animals mock-infected baculovirus lysates were less than 4 and the PRVN titers for the animals inoculated with the VLP particles were approximately 3000 following 4 injections with the VLP suspension of Example 10.

What is claimed is:

1. A bovine rotavirus protein selected from the group consisting of the VP7 protein of the IND strain, the VP7 protein of Cr strain, the VP7 protein of the 2292B strain and the VP7 protein of the WD653 strain.

2. The protein of claim 1 wherein the VP7 protein is from the IND strain of bovine rotavirus.

3. The protein of claim 1 wherein the VP7 protein is from the Cr strain of bovine rotavirus.

4. The protein of claim 1 wherein the VP7 protein is from the 2292B strain of bovine rotavirus.

5. The protein of claim 1 wherein the VP7 protein is from the WD653 strain of bovine rotavirus.

6. The protein of claim 1 wherein the VP7 protein comprises the amino acid sequence set forth in SEQ. ID. NO. 6.

7. The protein of claim 1 wherein the VP7 protein comprises the amino acid sequence set forth in SEQ. ID. NO. 7.

8. The protein of claim 1 wherein the VP7 protein comprises the amino acid sequence set forth in SEQ. ID. NO. 9.

* * * * *

SEQUENCE LISTING

```
<160> NUMBER OF SEQ ID NOS:   50

<210> SEQ ID NO 1
<211> LENGTH: 1062
<212> TYPE: DNA
<213> ORGANISM: Bovine rotavirus

<400> SEQUENCE: 1

ggctttaaaa gcgagaattt ccgtttggct agcggttacg tccttttaat gtatggtatt     60

gaatatacca caattctaat cttcttgaca tcagttacat tgctaaatta tatcttaaaa    120

tcaataacaa gagtaatgga ctatataatt tacagatttc tgcttatagt ggtaatcttg    180

gccaccatga taaatgcgca taattatgga gtgaatttgc caattacagg ttcaatggat    240

actgcatacg caaattcatc gcaaagtgag ccatttttaa catcaactct ttgtttgtat    300

tatcctgttg aggcatcaaa cgaaatagct gatactgaat ggaaagatac cttatcacta    360

atgttcttga caaaaggatg gccaacagga tcggtctact ttaaagaata tactgatata    420

gcggcttttt cagtagaacc acagctgtac tgtgattata atttagtttt aatgaaatat    480

gattctacac aggaactaga tatgtctgaa ttagccgatc ttatactgaa cgaatggctg    540

tgcaatccca tggacataac gttgtattat tatcagcaga ctgatgaagc aaataaatgg    600

atatcgatgg gctcttcttg cacagtcaaa gtgtgtccat taaatacgca gacacttggt    660

attggatgtc taataactaa tccagacacg tttgaaacag ttgcgacaac ggagaagttg    720

gtgattacag atgttgtaga tggtgtcaac tataagttaa acgtcacaac agcaacgtgt    780
```

-continued

```
accatacgca actgtcaaaa attaggacca agggagaatg tagctgtcat acaggtaggc    840

ggcgcgaata ttttagacat cacagctgat ccaacaacat caccacagac agagagaatg    900

atgcgaataa attggaaaaa atggtggcaa gtattctaca cagtggtgga ttatgtcaat    960

caaataattc aaacgatgtc caaaagatct agatcgctta actcgtcagc gttctattac   1020

agagtatagg tgcatgttag attagagttg tatgatgtga cc                      1062
```

<210> SEQ ID NO 2
<211> LENGTH: 1062
<212> TYPE: DNA
<213> ORGANISM: Bovine rotavirus

<400> SEQUENCE: 2

```
ggctttaaaa gcgagaattt ccgtttggct agcggttagc tccttttaat gtatggtatt     60

gaatatacca cattcctaat ctacttgata tcaattatat tacttaatta catattaaaa    120

agtataacta gaatgatgga gtacataatt tacaaatttt tgcttatagt cacaattact    180

tcaattgttg ttaatgcaca aaattacggt atcaatttac caataaccgg atcaatggat    240

acatcatatg tgaatgcacc taaagatgag ccatttctaa cgtcaacatt atgtttatac    300

tatccaacag aagctagaac agagataaac gataatgaga ggacaagtac gttgtcgcag    360

ctgttcttaa caaagggatg gccgactgga tccgtatact ttaaagaata tgatgatata    420

gctactttct cagtggatcc acaactgtat tgtgactata atatagttct gatcagatat    480

aattcgagcc tagaacttga tatgtcggaa ttagcaaatc taatattgaa tgaatggcta    540

tgcaatccaa tggacattac attgtattat taccaacaga cagacgaggc aaacatatgg    600

atagcaatgg gacaatcatg tactataaaa gtgtgtccat tgaataccca aacgctagga    660

ataggatgtc agactacaca tactggaacg tttgaagagg tcgcaacggc tgaaaaattg    720

gtaattactg atgtagttga cggcgtaaat cacaaactag atgttactac tgcgacctgt    780

actattagaa attgtaagaa attggggcca agagaaaatg tagcagtgat acaactgggt    840

ggtgctgata tccttgacat aacatctgat ccgacgacta atccacaaac tgaatggatg    900

atgcgaataa attggaagaa atggtggcaa gtgttctaca ctatagttga ttacgtgaac    960

caaattgtgc aagcaatgtc caagaggtcc agatcactga attcagcagc gttttattat   1020

agagtgtaga tattatgtag gttagagttg tatgatgtga cc                      1062
```

<210> SEQ ID NO 3
<211> LENGTH: 1063
<212> TYPE: DNA
<213> ORGANISM: Bovine rotavirus

<400> SEQUENCE: 3

```
ggcatttaaa aaagaaggag ctgtctgaca aactggtctt ctttttaaat ggtttgtaca     60

acattgtaca ccgtttgcgt gattctctgc attctgctaa tgtatataat actgttcaga    120

aaaatgattc attttctaat cgacttgtca cttattgctt ttgtaatatc aagttgcatc    180

agactgtcta atgctcagtt ttttgctaat gacatgcttt ataatggtaa tgttgaaggt    240

gtaattaata cgacaaatat ttttaatgtt gaatctcttt gcatttactt tccaaattct    300

gcagtggggc gacctggtcc agggaagagt gatggtttga ttaatgacaa caactacgct    360

caaacactag cagttctttt tgaaacaaaa ggatttccta aaggatcagt gaattttaat    420

acttatacta aaatatctga ctttataaat tcaattgaaa tgacatcttc ttataacata    480
```

-continued

```
gttataattc gtgaaactct agctaattct gaaacgattg aacaagtagc tgagtgggtc    540

cttaatgtgt ggaaatgtga caatatgaat gtggatattt atacttatga acaaataggg    600

aaagacaatt tttgggcggc atttggtgaa gattgtgatg ttgcggtatg tccactagac    660

acaacaatga atggtatcgg atgtacgcca gcaagtacag agacgtatga agtactatca    720

aatgacactc agttggccct tatagatgta gtggataatg tgaaacatag aatacaactg    780

aatcaagtaa cgtgtaaatt gagaaattgt gtgaaaggtg aagcaacact taacacagcg    840

attgtaagaa tttcgaactt gtccagtttt gataattcat tgtcaccatt gaataatggg    900

cagaagacaa gatcctttaa aattaatgcg aagaaatggt ggaaaatatt ctatactata    960

attgattaca ttaatacatt catacaatct atgacaccta ggcacagagc catttatccc   1020

gaaggatgga tgctgagata tgcgtaaacg agattatgtg gct                     1063
```

<210> SEQ ID NO 4
<211> LENGTH: 752
<212> TYPE: DNA
<213> ORGANISM: Bovine rotavirus

<400> SEQUENCE: 4

```
aaataatcag agatggcgtt cgctgcttgt gcaaaagctc aattagtgat tacaccaatg     60

cagcaatccg gagatttgtg tgctgcacgc tagtactgga atgtggatag tttcggacga    120

caactttaca aatatttttg aaacgtataa ttcagtaact ctatcctttt taccgtatga    180

tagcaccaac tatgatgtga ttgatattat atctaagaga gattattcac tgtgtcatat    240

attggcaata gatgtcataa agcctgaaat ggattttatt acgtttcttc aatcaaataa    300

tgaatgttca aaatatgcag ggcagaaaat agattatcaa aaactttcaa caaacgaaga    360

atggtttgtt tattcaaaga atttgaaatt ctgtccacta tctgacagcc taatcggatt    420

gtattgcgat acgcaggtaa gtggtacgta ttttccatta tcagagaatg aaaaatacga    480

tgttacggat ctaccagagt ttacagaaat gggttacgtc ttttattcga atgatgactt    540

ttatatttgt aaacgcatca atgaggataa taaatggtcg aattatcatc ttttttacag    600

agaatactcg gcatcaggga cggtgtcaag agctatcagt tgggacaacg tatggactgg    660

tttcaagaca ttcgcgcagg ttgtatataa aatactagat attttttca acaatagaag     720

gaactttttc tttattggct tcggcctact cg                                  752
```

<210> SEQ ID NO 5
<211> LENGTH: 2240
<212> TYPE: DNA
<213> ORGANISM: Bovine rotavirus

<400> SEQUENCE: 5

```
agcttaaaaa agtcaggatc aatggcgtcc tcactttacc gtcagctgat atcccagaac     60

tattattcaa ctggaaatga aatactactg gatcagcaaa caaacaaaac aactgttgat    120

tatgtagatg ctgggaatta cacatatgcc cagttaccac caacaacgtg gggagcagag    180

tcgacatatg aatctgcatt cagcgcgcca gagataactg gaccatatac aaatacagtc    240

ataaaattga gtgatctatc agattcgaac gtatgggtat tatatcagaa accaactagc    300

acagttaaat tgcttaaaaa tggaccagaa agttatagtt ggaaccttgc agcatttgaa    360

ttatggtatg gaaaggcaaa tacaacggtt acatcagatt actattcagg gatgacaaat    420

tctgaaaaaa gtgttgaggt agatcatgat tcactagtac tattttggaa tgaaggctca    480

acagcattaa gtaacaaagt gatcaatttt tcctggaatg ttggtggcgt gttaattaaa    540
```

-continued

```
ctaacaagta atacaaggat agacatatgc atggctaaca tggataattt tactagtgat    600

agcttcaatt gggaagaatg gacacataat tttcctcgca gtgcgagcat gaacatttat    660

actgattact acttagctag tgtagatcca tatagtcaaa taagagcatt acagcaacca    720

ataataacaa ctgttgaaat gaagatggtg aaagttaaga gagaaggatc aattaatgta    780

gatgaagttg taagtaagga ttcattatgg caagaggtaa ggtacgttag agatataaca    840

cttcagtgta aaattgagtc tgaagttgtt aaaggtggtg gatggggtta tgactatact    900

agcgtagcct ttaaaaccat taatcacacg tactcttata ctagagcagg agaggctgtt    960

aatgcgcacg ttacaattag ttttaacaat ttgaaggaac gctcatatgg agggtcatta   1020

ccaactgatt tcaaaattgg acggttcgac ataatagacg ttgatacata catgtacata   1080

gattattggg atgactcaga aatctttaaa aatatggtgt atgtgcgtga tttgagagct   1140

gatatgggtg gatttaatta ctcgtcagcc atgtcatact actttagaat tcccgttggg   1200

cagtatcctg ggttgcattc atcaggagta agatttacat atgagaggag tctattatct   1260

caacaattta ctgatcaggt agcgcttaat tcaatgagat ttgtgttcag agcaacatca   1320

tcagatggtt ggtttatgac agcaggaaat ataaatgcaa gacgtatagc gtctggaaca   1380

ggatttgcat attcggatgg ttatgttact gaaactgttg ggacggtttc gtttatatca   1440

ttaattccaa gcaatccaaa ttatcagaca ccaatagctt catcaagtac agtgagaatg   1500

gatttagaac ggaagattaa cgatctacgt aatgatttca atgaattggc tagttctgtt   1560

gcactaggtg acatactatc actagcaatg tctccattga cctttgctaa tctacttgaa   1620

tctgttccag caattgcatc atctgtgaaa gatgttgcgg gaaacgtcat gaaaaagttt   1680

aaaacgacga aatgtttaa aaaagctgca aagccaaagt ataaggaata tattatcgga   1740

gacttgctag aagatgtgac aaatcttcca agaagtacta ccgcaatgga ttttgatgat   1800

attacatcag cagtaatggt ttcaacaaca aacaggttgc agcttacaga tgtagaaacg   1860

ctgtcagaaa ttgtagccag atcagcagat gatttcatac ccaatagagc gtatagaatg   1920

atagaggatg gtatggtgca cgaagcaaca cctaatggag ttttttctta tgatttggct   1980

actctgcagc agaggaattt tgacatggaa aaattcatgc agcttgcgtc aaaatcacca   2040

gtaatatcag caatagtaga ctttgcaaca ttaaaggcta tgagagatac atatggcgtt   2100

agtacagaca ttatgtataa actagtggca tcagatgctc cgacaatagt atcattcatt   2160

aataataaca atccgctgat tagaaataga atagaaggat tgttgagaca atgtagaata   2220

taaaaagtgg ggagatcgac                                               2240
```

<210> SEQ ID NO 6
<211> LENGTH: 326
<212> TYPE: PRT
<213> ORGANISM: Bovine rotavirus

<400> SEQUENCE: 6

```
Met Tyr Gly Ile Glu Tyr Thr Thr Ile Leu Ile Phe Leu Thr Ser Val
1               5                   10                  15

Thr Leu Leu Asn Tyr Ile Leu Lys Ser Ile Thr Arg Val Met Asp Tyr
            20                  25                  30

Ile Ile Tyr Arg Phe Leu Leu Ile Val Val Ile Leu Ala Thr Met Ile
        35                  40                  45

Asn Ala His Asn Tyr Gly Val Asn Leu Pro Ile Thr Gly Ser Met Asp
    50                  55                  60
```

-continued

```
Thr Ala Tyr Ala Asn Ser Ser Gln Ser Glu Pro Phe Leu Thr Ser Thr
65                  70                  75                  80

Leu Cys Leu Tyr Tyr Pro Val Glu Ala Ser Asn Glu Ile Ala Asp Thr
                85                  90                  95

Glu Trp Lys Asp Thr Leu Ser Leu Met Phe Leu Thr Lys Gly Trp Pro
            100                 105                 110

Thr Gly Ser Val Tyr Phe Lys Glu Tyr Thr Asp Ile Ala Ala Phe Ser
        115                 120                 125

Val Glu Pro Gln Leu Tyr Cys Asp Tyr Asn Leu Val Leu Met Lys Tyr
    130                 135                 140

Asp Ser Thr Gln Glu Leu Asp Met Ser Glu Leu Ala Asp Leu Ile Leu
145                 150                 155                 160

Asn Glu Trp Leu Cys Asn Pro Met Asp Ile Thr Leu Tyr Tyr Tyr Gln
                165                 170                 175

Gln Thr Asp Glu Ala Asn Lys Trp Ile Ser Met Gly Ser Ser Cys Thr
            180                 185                 190

Val Lys Val Cys Pro Leu Asn Thr Gln Thr Leu Gly Ile Gly Cys Leu
        195                 200                 205

Ile Thr Asn Pro Asp Thr Phe Glu Thr Val Ala Thr Thr Glu Lys Leu
    210                 215                 220

Val Ile Thr Asp Val Val Asp Gly Val Asn Tyr Lys Leu Asn Val Thr
225                 230                 235                 240

Thr Ala Thr Cys Thr Ile Arg Asn Cys Gln Lys Leu Gly Pro Arg Glu
                245                 250                 255

Asn Val Ala Val Ile Gln Val Gly Gly Ala Asn Ile Leu Asp Ile Thr
            260                 265                 270

Ala Asp Pro Thr Thr Ser Pro Gln Thr Glu Arg Met Met Arg Ile Asn
        275                 280                 285

Trp Lys Lys Trp Trp Gln Val Phe Tyr Thr Val Val Asp Tyr Val Asn
    290                 295                 300

Gln Ile Ile Gln Thr Met Ser Lys Arg Ser Arg Ser Leu Asn Ser Ser
305                 310                 315                 320

Ala Phe Tyr Tyr Arg Val
                325


<210> SEQ ID NO 7
<211> LENGTH: 326
<212> TYPE: PRT
<213> ORGANISM: Bovine rotavirus
<220> FEATURE:
<221> NAME/KEY: LIPID
<222> LOCATION: (208)..(208)
<223> OTHER INFORMATION: any of the naturrally occurring amino acids

<400> SEQUENCE: 7

Met Tyr Gly Ile Glu Tyr Thr Thr Phe Leu Ile Tyr Leu Ile Ser Ile
1               5                   10                  15

Ile Leu Leu Asn Tyr Ile Leu Lys Ser Ile Thr Arg Met Met Glu Tyr
            20                  25                  30

Ile Ile Tyr Lys Phe Leu Leu Ile Val Thr Ile Thr Ser Ile Val Val
        35                  40                  45

Asn Ala Gln Asn Tyr Gly Ile Asn Leu Pro Ile Thr Gly Ser Met Asp
    50                  55                  60

Thr Ser Tyr Val Asn Ala Pro Lys Asp Glu Pro Phe Leu Thr Ser Thr
65                  70                  75                  80

Leu Cys Leu Tyr Tyr Pro Thr Glu Ala Arg Thr Glu Ile Asn Asp Asn
```

-continued 85 90 95

Glu Arg Thr Ser Thr Leu Ser Gln Leu Phe Leu Thr Lys Gly Trp Pro
100 105 110

Thr Gly Ser Val Tyr Phe Lys Glu Tyr Asp Asp Ile Ala Thr Phe Ser
115 120 125

Val Asp Pro Gln Leu Tyr Cys Asp Tyr Asn Ile Val Leu Met Arg Tyr
130 135 140

Asn Ser Ser Leu Glu Leu Asp Met Ser Glu Leu Ala Asn Leu Ile Leu
145 150 155 160

Asn Glu Trp Leu Cys Asn Pro Met Asp Ile Thr Leu Tyr Tyr Tyr Gln
165 170 175

Gln Thr Asp Glu Ala Asn Ile Trp Ile Ala Met Gly Gln Ser Cys Thr
180 185 190

Ile Lys Val Cys Pro Leu Asn Thr Gln Thr Leu Gly Ile Gly Cys Xaa
195 200 205

Thr Thr His Thr Gly Thr Phe Glu Glu Val Ala Thr Ala Glu Lys Leu
210 215 220

Val Ile Thr Asp Val Val Asp Gly Val Asn His Lys Leu Asp Val Thr
225 230 235 240

Thr Ala Thr Cys Thr Ile Arg Asn Cys Lys Lys Leu Gly Pro Arg Glu
245 250 255

Asn Val Ala Val Ile Gln Val Gly Gly Ala Asp Ile Leu Asp Ile Thr
260 265 270

Ser Asp Pro Thr Thr Asn Pro Gln Thr Glu Trp Met Met Arg Ile Asn
275 280 285

Trp Lys Lys Trp Trp Gln Val Phe Tyr Thr Ile Val Asp Tyr Val Asn
290 295 300

Gly Ile Val Gln Ala Met Ser Lys Arg Ser Arg Ser Leu Asn Ser Ala
305 310 315 320

Ala Phe Tyr Tyr Arg Val
325

<210> SEQ ID NO 8
<211> LENGTH: 332
<212> TYPE: PRT
<213> ORGANISM: Bovine rotavirus
<220> FEATURE:
<221> NAME/KEY: LIPID
<222> LOCATION: (50)..(50)
<223> OTHER INFORMATION: any of the naturrally occurring amino acids
<221> NAME/KEY: LIPID
<222> LOCATION: (246)..(246)
<223> OTHER INFORMATION: any of the naturrally ocurring amino acids

<400> SEQUENCE: 8

Met Val Cys Thr Thr Leu Tyr Thr Val Cys Val Ile Leu Cys Ile Leu
1 5 10 15

Leu Met Tyr Ile Ile Leu Phe Arg Lys Met Ile His Phe Leu Ile Asp
20 25 30

Leu Ser Leu Ile Ala Phe Val Ile Ser Ser Cys Ile Arg Leu Ser Asn
35 40 45

Ala Xaa Phe Phe Ala Asn Asp Met Leu Tyr Asn Gly Asn Val Glu Gly
50 55 60

Val Ile Asn Thr Thr Asn Ile Phe Asn Val Glu Ser Leu Cys Ile Tyr
65 70 75 80

Phe Pro Asn Ser Ala Val Gly Arg Pro Gly Pro Gly Lys Ser Asp Gly
85 90 95

-continued

```
Leu Ile Asn Asp Asn Asn Tyr Ala Gln Thr Leu Ala Val Leu Phe Glu
            100                 105                 110

Thr Lys Gly Phe Pro Lys Gly Ser Val Asn Phe Asn Thr Tyr Thr Lys
        115                 120                 125

Ile Ser Asp Phe Ile Asn Ser Ile Glu Met Thr Cys Ser Tyr Asn Ile
    130                 135                 140

Val Ile Ile Pro Glu Thr Leu Ala Asn Ser Glu Thr Ile Glu Gln Val
145                 150                 155                 160

Ala Glu Trp Val Leu Asn Phe Trp Lys Cys Asp Asn Met Asn Val Asp
                165                 170                 175

Ile Tyr Thr Tyr Glu Gln Ile Gly Lys Asp Asn Phe Trp Ala Ala Phe
            180                 185                 190

Gly Glu Asp Cys Asp Val Ala Val Cys Pro Leu Asp Thr Thr Met Asn
        195                 200                 205

Gly Ile Gly Cys Thr Pro Ala Ser Thr Glu Thr Tyr Glu Val Leu Ser
    210                 215                 220

Asn Asp Thr Gln Leu Ala Leu Ile Asp Val Val Asp Asn Val Lys His
225                 230                 235                 240

Arg Ile Gln Leu Asn Xaa Val Thr Cys Lys Leu Arg Asn Cys Val Lys
                245                 250                 255

Gly Glu Ala Arg Leu Asn Thr Ala Ile Val Arg Ile Ser Asn Leu Ser
            260                 265                 270

Ser Phe Asp Asn Ser Leu Ser Pro Leu Asn Asn Gly Gln Lys Thr Arg
        275                 280                 285

Ser Phe Lys Ile Asn Ala Lys Lys Trp Trp Lys Ile Phe Tyr Thr Ile
    290                 295                 300

Ile Asp Tyr Ile Asn Thr Phe Ile Gln Ser Met Thr Pro Arg His Arg
305                 310                 315                 320

Ala Ile Tyr Pro Glu Gly Trp Met Leu Arg Tyr Ala
                325                 330


<210> SEQ ID NO 9
<211> LENGTH: 248
<212> TYPE: PRT
<213> ORGANISM: Bovine rotavirus

<400> SEQUENCE: 9

Met Ala Phe Ile Ala Ser Arg Leu Ala Ala Cys Ala Lys Ala Gln Leu
1               5                   10                  15

Val Ile Thr Pro Ile Ser Asn Pro Glu Ile Cys Val Leu His Ala Ser
            20                  25                  30

Thr Gly Met Trp Ile Val Ser Asp Asp Asn Phe Thr Asn Ile Phe Glu
        35                  40                  45

Thr Tyr Asn Ser Val Thr Leu Ser Phe Leu Pro Tyr Asp Ser Thr Asn
    50                  55                  60

Tyr Asp Val Ile Asp Ile Ile Ser Lys Arg Asp Tyr Ser Leu Cys His
65                  70                  75                  80

Ile Leu Ala Ile Asp Val Ile Lys Pro Glu Met Asp Phe Ile Thr Phe
                85                  90                  95

Leu Gln Ser Asn Asn Glu Cys Ser Lys Tyr Ala Gly Gln Lys Ile Asp
            100                 105                 110

Tyr Gln Lys Leu Ser Thr Asn Glu Glu Trp Phe Val Tyr Ser Lys Asn
        115                 120                 125

Leu Lys Phe Cys Pro Leu Ser Asp Ser Leu Ile Gly Leu Tyr Cys Asp
```

-continued

```
    130                 135                 140

Thr Gln Val Ser Gly Thr Tyr Phe Pro Leu Ser Glu Asn Glu Lys Tyr
145                 150                 155                 160

Asp Val Thr Asp Leu Pro Glu Phe Thr Glu Met Gly Tyr Val Phe Tyr
                165                 170                 175

Ser Asn Asp Asp Phe Tyr Ile Cys Lys Arg Ile Asn Glu Asp Asn Lys
            180                 185                 190

Trp Ser Asn Tyr His Leu Phe Tyr Arg Glu Tyr Ser Ala Ser Gly Thr
        195                 200                 205

Val Ser Arg Ala Ile Ser Trp Asp Asn Val Trp Thr Gly Phe Lys Thr
    210                 215                 220

Phe Ala Gln Val Val Tyr Lys Ile Leu Asp Ile Phe Phe Asn Asn Arg
225                 230                 235                 240

Arg Asn Pro Gly Pro Arg Ala Met
                245


<210> SEQ ID NO 10
<211> LENGTH: 733
<212> TYPE: PRT
<213> ORGANISM: Bovine rotavirus

<400> SEQUENCE: 10

Met Ala Ser Ser Leu Tyr Arg Gln Leu Ile Ser Gln Asn Tyr Tyr Ser
1               5                   10                  15

Thr Gly Asn Glu Ile Leu Leu Asp Gln Gln Thr Asn Lys Thr Thr Val
            20                  25                  30

Asp Tyr Val Asp Ala Gly Asn Tyr Thr Tyr Ala Gln Leu Pro Pro Thr
        35                  40                  45

Thr Trp Gly Ala Glu Ser Thr Tyr Glu Ser Ala Phe Ser Ala Pro Glu
    50                  55                  60

Ile Thr Gly Pro Tyr Thr Asn Thr Val Ile Lys Leu Ser Asp Leu Ser
65                  70                  75                  80

Asp Ser Asn Val Trp Val Leu Tyr Gln Lys Pro Thr Ser Thr Val Lys
                85                  90                  95

Leu Leu Lys Asn Gly Pro Glu Ser Tyr Ser Trp Asn Leu Ala Ala Phe
            100                 105                 110

Glu Leu Trp Tyr Gly Lys Ala Asn Thr Thr Val Thr Ser Asp Tyr Tyr
        115                 120                 125

Ser Gly Met Thr Asn Ser Glu Lys Ser Val Glu Val Asp His Asp Ser
    130                 135                 140

Leu Val Leu Phe Trp Asn Glu Gly Ser Thr Ala Leu Ser Asn Lys Val
145                 150                 155                 160

Ile Asn Phe Ser Trp Asn Val Gly Gly Val Leu Ile Lys Leu Thr Ser
                165                 170                 175

Asn Thr Arg Ile Asp Ile Cys Met Ala Asn Met Asp Asn Phe Thr Ser
            180                 185                 190

Asp Ser Phe Asn Trp Glu Glu Trp Thr His Asn Phe Pro Arg Ser Ala
        195                 200                 205

Ser Met Asn Ile Tyr Thr Asp Tyr Tyr Leu Ala Ser Val Asp Pro Tyr
    210                 215                 220

Ser Gln Ile Arg Ala Leu Gln Gln Pro Ile Ile Thr Thr Val Glu Met
225                 230                 235                 240

Lys Met Val Lys Val Lys Arg Glu Gly Ser Ile Asn Val Asp Glu Val
                245                 250                 255
```

-continued

```
Val Ser Lys Asp Ser Leu Trp Gln Glu Val Arg Tyr Val Arg Asp Ile
            260                 265                 270

Thr Leu Gln Cys Lys Ile Glu Ser Glu Val Val Lys Gly Gly Gly Trp
        275                 280                 285

Gly Tyr Asp Tyr Thr Ser Val Ala Phe Lys Thr Ile Asn His Thr Tyr
    290                 295                 300

Ser Tyr Thr Arg Ala Gly Glu Ala Val Asn Ala His Val Thr Ile Ser
305                 310                 315                 320

Phe Asn Asn Leu Lys Glu Arg Ser Tyr Gly Gly Ser Leu Pro Thr Asp
                325                 330                 335

Phe Lys Ile Gly Arg Phe Asp Ile Ile Asp Val Asp Thr Tyr Met Tyr
            340                 345                 350

Ile Asp Tyr Trp Asp Asp Ser Glu Ile Phe Lys Asn Met Val Tyr Val
        355                 360                 365

Arg Asp Leu Arg Ala Asp Met Gly Gly Phe Asn Tyr Ser Ser Ala Met
    370                 375                 380

Ser Tyr Tyr Phe Arg Ile Pro Val Gly Gln Tyr Pro Gly Leu His Ser
385                 390                 395                 400

Ser Gly Val Arg Phe Thr Tyr Glu Arg Ser Leu Leu Ser Gln Gln Phe
                405                 410                 415

Thr Asp Gln Val Ala Leu Asn Ser Met Arg Phe Val Phe Arg Ala Thr
            420                 425                 430

Ser Ser Asp Gly Trp Phe Met Thr Ala Gly Asn Ile Asn Ala Arg Arg
        435                 440                 445

Ile Ala Ser Gly Thr Ser Phe Ala Tyr Ser Asp Gly Thr Val Thr Glu
    450                 455                 460

Thr Val Gly Thr Val Ser Phe Ile Ser Leu Ile Pro Ser Asn Pro Asn
465                 470                 475                 480

Tyr Gln Thr Pro Ile Ala Ser Ser Ser Thr Val Arg Met Asp Leu Glu
                485                 490                 495

Arg Lys Ile Asn Asp Leu Arg Asn Asp Phe Asn Glu Leu Ala Ser Ser
            500                 505                 510

Val Ala Leu Gly Asp Ile Leu Ser Leu Ala Met Ser Pro Leu Thr Phe
        515                 520                 525

Ala Asn Leu Leu Glu Ser Val Pro Ala Ile Ala Ser Ser Val Lys Asp
    530                 535                 540

Val Ala Ala Asn Val Met Lys Lys Phe Lys Thr Thr Lys Met Phe Lys
545                 550                 555                 560

Lys Ala Ala Lys Pro Lys Tyr Lys Glu Tyr Ile Ile Gly Asp Leu Leu
                565                 570                 575

Glu Asp Val Thr Asn Leu Pro Arg Ser Thr Thr Ala Met Asp Phe Asp
            580                 585                 590

Asp Ile Thr Ser Ala Val Met Val Ser Thr Thr Asn Arg Leu Gln Leu
        595                 600                 605

Thr Asp Val Glu Thr Leu Ser Glu Ile Val Ala Arg Ser Ala Asp Asp
    610                 615                 620

Phe Ile Pro Asn Arg Ala Tyr Arg Met Ile Glu Asp Gly Met Val His
625                 630                 635                 640

Glu Ala Thr Pro Asn Gly Val Phe Ser Tyr Asp Leu Ala Thr Leu Gln
                645                 650                 655

Gln Arg Asn Phe Asp Met Glu Lys Phe Met Gln Leu Ala Ser Lys Ser
            660                 665                 670

Pro Val Ile Ser Ala Ile Val Asp Phe Ala Thr Leu Lys Ala Met Arg
```

-continued

```
        675                 680                 685

Asp Thr Tyr Gly Val Ser Thr Asp Ile Met Tyr Lys Leu Val Ala Ser
    690                 695                 700

Asp Ala Pro Thr Ile Val Ser Phe Ile Asn Asn Asn Asn Pro Leu Ile
705                 710                 715                 720

Arg Asn Arg Ile Glu Gly Leu Leu Arg Gln Cys Arg Ile
                725                 730


<210> SEQ ID NO 11
<211> LENGTH: 2363
<212> TYPE: DNA
<213> ORGANISM: Bovine rotavirus
<220> FEATURE:
<221> NAME/KEY: misc_feature
<222> LOCATION: (323)..(323)
<223> OTHER INFORMATION: n = a, g, c, or t

<400> SEQUENCE: 11

ggctataaaa tggcttggct catatacaga cagctgctcg atcattctta cgcagtagat      60

ttatctgatg agatacagtc agttggatca gagaagaacc aacgcgttac agtgaatcca     120

ggaccatttg cgcagacagg atatgcgcca gtgaactggg ggcccggtga agtgaatgac     180

tcgactgtag tacaacctgt gtcggatgga ccgtatcaac cagcgtcgtt tgatctacca     240

gtaggaaatt ggatgttgtt agcgccaaca ggaccaggtg tggtagtgga aggaacagac     300

aattctggca gatggttatc cgnaattcta attgagccag gtgtcacatc agagacaaga     360

acgtatacga tgtttggatc aagtaaacag atgttagtgt cgaacgtgtc tgatacgaaa     420

tggaaatttg ttgaaatgat gaaggcggag gttgatggtg actatgcgga gtggggaaca     480

ttattatcgg acaccaagct ctatgggatg atgaaatatg gggagagact attcatatac     540

gaaggagaaa ccccaaatgc cacgaccaac ggatacatcg taacgaatta tgcatcagtt     600

gaggtaaggc catatagtga cttttatata atttccagat cacaggagtc ggagtgcact     660

gaatatataa acaacgggct gccacccatt caaaatacca gaaatgtagt gcctgtggca     720

atatcgtcaa gatcaattaa accaagagaa gtccaagcta atgaagatat tgtagtttct     780

aaaacctcac tatggaaaga aatgcaatat aatagagata tcataattag attcaagttt     840

gataactcga taataaaatc tggaggtttg ggctataagt gggctgaaat ctcatttaaa     900

gctgcaaatt atcaatacaa ttacataaga gacggagaag aagtcacagc gcatacgacg     960

tgctcagtta atggtcttaa tgattttagc tttaacggag gctcattacc aacggatttc    1020

gcaatatcga gatatgaagt aattaaagaa aattcgtatg tatacgtgga ctactgggac    1080

gattcacaag catccaggaa tctggtctac gtactattat tagcagcgaa tttgaatgac    1140

gtaatgtgtt ctggtggaga ttatagcttc gctttacctg ttccacagtg gccactgatc    1200

aaaccaggga cggtgacgtt gcacacagcg ggagtaacat tatctacaca attcaccgac    1260

ttcgtatcac tgaattcact aagatttagg tttagactgg cggtcgagga accctcattc    1320

acgataacca gaacacgtgt gtcaaagccg tatggcctac cagcagccaa cccaaacggc    1380

ggaaaagagt cctatgaagt ggctggaagg tttccgttca attcattggt gccatcaaat    1440

gacgattacc caacgccaat tacgaactca gtaacagtaa ggcaagcatt ggaaaggcgc    1500

ttaaatgaat cgagagaaga attcaataac ttgtcacaag agacagccgt gtcacagtta    1560

attgacttag ctatgtggcc actagacatg tttccgatgt tctcggaaat tgagagtacc    1620

gtgattgcag caaaaccaat ggctaccaat gtgatgagga agcttaagag ttcaaaactc    1680
```

-continued

```
gcgtcaccag tgtcgatgtt aagcgactct ttatccgatg cggcctactc tatcgcaaga   1740

agtacaccag tacgatcaat aggaccaaca gcatcacgtt gggctaatat tccagaacag   1800

acacaagacg ctgttagtga agttgccaca atatcatcac aagtgtcaca aataagtcca   1860

aaattaagat tgaaagaaat tccgactcca acagagggat tgaatttcga tgacatatca   1920

cggcggtatt caaaagccaa gatagaaaga tcaatacagg tcgccccaaa tgcattacca   1980

gacgtcatca cagaagcgtc agagaaattc atccgtaata gggcgtatag agtaatagac   2040

ggggatgaag catttgaggc gggcactgac ggaagatttt tcgcgtacag ggtggaaacg   2100

cttgaggaaa tgccattcaa tatagaaaaa tttgcagact tagttaccaa ctcaccagtg   2160

atatcagcaa taatagactt taagacattg aaaaacctga atgacaatta tgggataact   2220

agagagcaag catttagttt gttacggtca gacccaaaag ttttgcgtgg atttatcgcc   2280

caaaacaatc caattataaa aaataggata gaacagttga tcatgcaatg tagattgtga   2340

gcagcttctg gaggatgtga acc                                           2363
```

<210> SEQ ID NO 12
<211> LENGTH: 475
<212> TYPE: DNA
<213> ORGANISM: Bovine rotavirus

<400> SEQUENCE: 12

```
ccatatacac cagatagttc attcttgcca tctaactatt ggtatttagt caatccatcg     60

aatgacggtg tggcgttctc agtaacggat aacagcacgt cttggatgtt tacttatcta    120

gccttaccaa atacagctca gactaatgtc acagtaaatg tgttgaatga gacagtgaat    180

atatcaatag acaattcggg ctcgacatat aggtttgtgg attacattaa gactagctcc    240

acacaagcgt atggatcgag gaactatcta aatactgcac atagattaca agcttacaga    300

agagatggag atggaaatat atcaaattat tggggtgcgg atacacaagg tgacttaagg    360

gttgggacat attctaatcc ggtgccaaat gcagtgatca atctaaatgc agatttttac    420

gtcataccag attcgcaaca agagatatgt acagaataca taaggggagg attgc         475
```

<210> SEQ ID NO 13
<211> LENGTH: 13
<212> TYPE: DNA
<213> ORGANISM: Bovine rotavirus

<400> SEQUENCE: 13

```
ggctattaaa ggt                                                        13
```

<210> SEQ ID NO 14
<211> LENGTH: 15
<212> TYPE: DNA
<213> ORGANISM: Bovine rotavirus

<400> SEQUENCE: 14

```
ggtcatatct ccaca                                                      15
```

<210> SEQ ID NO 15
<211> LENGTH: 36
<212> TYPE: DNA
<213> ORGANISM: Bovine rotavirus

<400> SEQUENCE: 15

```
cccgggatcc gaattcggct ataaaatggc ttggct                               36
```

-continued

<210> SEQ ID NO 16
<211> LENGTH: 33
<212> TYPE: DNA
<213> ORGANISM: Bovine rotavirus

<400> SEQUENCE: 16
tcgcgaattc tgcaggtaca tcctccagaa gct 33

<210> SEQ ID NO 17
<211> LENGTH: 17
<212> TYPE: DNA
<213> ORGANISM: Bovine rotavirus

<400> SEQUENCE: 17
ggcttttaaa cgaagtc 17

<210> SEQ ID NO 18
<211> LENGTH: 18
<212> TYPE: DNA
<213> ORGANISM: Bovine rotavirus

<400> SEQUENCE: 18
ggtcacatcc tctcacta 18

<210> SEQ ID NO 19
<211> LENGTH: 36
<212> TYPE: DNA
<213> ORGANISM: Bovine rotavirus

<400> SEQUENCE: 19
cccgggatcc atggccggct ttaaaagcga gaattt 36

<210> SEQ ID NO 20
<211> LENGTH: 24
<212> TYPE: DNA
<213> ORGANISM: Bovine rotavirus

<400> SEQUENCE: 20
cgatcgcgaa ttctgcggca ggtc 24

<210> SEQ ID NO 21
<211> LENGTH: 19
<212> TYPE: DNA
<213> ORGANISM: Bovine rotavirus

<400> SEQUENCE: 21
ggaaatatca gagatgcgt 19

<210> SEQ ID NO 22
<211> LENGTH: 19
<212> TYPE: DNA
<213> ORGANISM: Bovine rotavirus

<400> SEQUENCE: 22
ttctttatgc ttcggccta 19

<210> SEQ ID NO 23
<211> LENGTH: 19
<212> TYPE: DNA
<213> ORGANISM: Bovine rotavirus

<400> SEQUENCE: 23
ggaaatatca gagatgcgt 19

-continued

<210> SEQ ID NO 24
<211> LENGTH: 19
<212> TYPE: DNA
<213> ORGANISM: Bovine rotavirus

<400> SEQUENCE: 24
ttctttatgc ttcggccta 19

<210> SEQ ID NO 25
<211> LENGTH: 20
<212> TYPE: DNA
<213> ORGANISM: Bovine rotavirus

<400> SEQUENCE: 25
gcatttaaaa tctcattcac 20

<210> SEQ ID NO 26
<211> LENGTH: 20
<212> TYPE: DNA
<213> ORGANISM: Bovine rotavirus

<400> SEQUENCE: 26
agccacatag ttcacatttc 20

<210> SEQ ID NO 27
<211> LENGTH: 23
<212> TYPE: DNA
<213> ORGANISM: Bovine rotavirus

<400> SEQUENCE: 27
gcatttaaaa aagaagaagc tgt 23

<210> SEQ ID NO 28
<211> LENGTH: 22
<212> TYPE: DNA
<213> ORGANISM: Bovine rotavirus

<400> SEQUENCE: 28
agccacatga tcttgtttac gc 22

<210> SEQ ID NO 29
<211> LENGTH: 20
<212> TYPE: DNA
<213> ORGANISM: Bovine rotavirus

<400> SEQUENCE: 29
ccgtatcagc cggcgccgtt 20

<210> SEQ ID NO 30
<211> LENGTH: 20
<212> TYPE: DNA
<213> ORGANISM: Bovine rotavirus

<400> SEQUENCE: 30
ggcggcagcc cgttgtttat 20

<210> SEQ ID NO 31
<211> LENGTH: 21
<212> TYPE: DNA
<213> ORGANISM: Bovine rotavirus

<400> SEQUENCE: 31
gtatggtatt gaatatacca c 21

-continued

<210> SEQ ID NO 32
<211> LENGTH: 17
<212> TYPE: DNA
<213> ORGANISM: Bovine rotavirus

<400> SEQUENCE: 32
gatcctgttg gccatcc 17

<210> SEQ ID NO 33
<211> LENGTH: 20
<212> TYPE: DNA
<213> ORGANISM: Bovine rotavirus

<400> SEQUENCE: 33
ggcttaaaaa agtcaggatc 20

<210> SEQ ID NO 34
<211> LENGTH: 18
<212> TYPE: DNA
<213> ORGANISM: Bovine rotavirus

<400> SEQUENCE: 34
tcagaatttg tcatccct 18

<210> SEQ ID NO 35
<211> LENGTH: 18
<212> TYPE: DNA
<213> ORGANISM: Bovine rotavirus

<400> SEQUENCE: 35
aatgttcatg ctcgcact 18

<210> SEQ ID NO 36
<211> LENGTH: 17
<212> TYPE: DNA
<213> ORGANISM: Bovine rotavirus

<400> SEQUENCE: 36
ccaagaagta ctaccgc 17

<210> SEQ ID NO 37
<211> LENGTH: 18
<212> TYPE: DNA
<213> ORGANISM: Bovine rotavirus

<400> SEQUENCE: 37
cttatgattt ggctactc 18

<210> SEQ ID NO 38
<211> LENGTH: 20
<212> TYPE: DNA
<213> ORGANISM: Bovine rotavirus

<400> SEQUENCE: 38
agccacataa taagtcgatc 20

<210> SEQ ID NO 39
<211> LENGTH: 20
<212> TYPE: DNA
<213> ORGANISM: Bovine rotavirus

<400> SEQUENCE: 39

-continued ggcatttaaa aaagaagaag 20

<210> SEQ ID NO 40
<211> LENGTH: 19
<212> TYPE: DNA
<213> ORGANISM: Bovine rotavirus

<400> SEQUENCE: 40
caaaagcaat aagtgacaa 19

<210> SEQ ID NO 41
<211> LENGTH: 776
<212> TYPE: PRT
<213> ORGANISM: Bovine rotavirus
<220> FEATURE:
<221> NAME/KEY: LIPID
<222> LOCATION: (105)..(105)
<223> OTHER INFORMATION: x = any of the naturrally occurring amino acids

<400> SEQUENCE: 41

```
Met Ala Trp Leu Ile Tyr Arg Gln Leu Leu Asp Asn Ser Tyr Ala Val
1               5                   10                  15

Asp Leu Ser Asp Glu Ile Gln Ser Val Gly Ser Glu Lys Asn Gln Arg
            20                  25                  30

Val Thr Val Asn Pro Gly Pro Phe Ala Gln Thr Gly Tyr Ala Pro Val
        35                  40                  45

Asn Trp Gly Pro Gly Glu Val Asn Asp Ser Thr Val Val Gln Pro Val
    50                  55                  60

Ser Asp Gly Pro Tyr Gln Pro Ala Ser Phe Asp Leu Pro Val Gly Asn
65                  70                  75                  80

Trp Met Leu Leu Ala Pro Thr Gly Pro Gly Val Val Val Glu Gly Thr
                85                  90                  95

Asp Asn Ser Gly Arg Trp Leu Ser Xaa Ile Leu Ile Glu Pro Gly Val
            100                 105                 110

Thr Ser Glu Thr Arg Thr Tyr Thr Met Phe Gly Ser Ser Lys Gln Met
        115                 120                 125

Leu Val Ser Asn Tyr Ser Asp Thr Lys Trp Lys Phe Val Glu Met Met
    130                 135                 140

Lys Ala Glu Val Asp Gly Asp Tyr Ala Glu Trp Gly Thr Leu Leu Ser
145                 150                 155                 160

Asp Thr Lys Leu Tyr Gly Met Met Lys Tyr Gly Glu Arg Leu Phe Ile
                165                 170                 175

Tyr Glu Gly Glu Thr Pro Asn Ala Thr Thr Asn Gly Tyr Ile Val Thr
            180                 185                 190

Asn Tyr Ala Ser Val Glu Val Arg Pro Tyr Ser Asp Phe Tyr Ile Ile
        195                 200                 205

Ser Arg Ser Gln Glu Ser Glu Cys Thr Glu Tyr Ile Asn Asn Gly Leu
    210                 215                 220

Pro Pro Ile Gln Asn Thr Arg Asn Val Val Pro Val Ala Ile Ser Ser
225                 230                 235                 240

Arg Ser Ile Lys Pro Arg Glu Val Gln Ala Asn Glu Asp Ile Val Val
                245                 250                 255

Ser Lys Thr Ser Leu Trp Lys Glu Met Gln Tyr Asn Arg Asp Ile Ile
            260                 265                 270

Ile Arg Phe Lys Phe Asp Asn Ser Ile Ile Lys Ser Gly Gly Leu Gly
        275                 280                 285

Tyr Lys Trp Ala Glu Ile Ser Phe Lys Ala Ala Asn Tyr Gln Tyr Asn
```

-continued

```
    290                 295                 300

Tyr Ile Arg Asp Gly Glu Glu Val Thr Ala His Thr Thr Cys Ser Val
305                 310                 315                 320

Asn Gly Leu Asn Asp Phe Ser Phe Asn Gly Gly Ser Leu Pro Thr Asp
                325                 330                 335

Phe Ala Ile Ser Arg Tyr Glu Val Ile Lys Glu Asn Ser Tyr Val Tyr
            340                 345                 350

Val Asp Tyr Trp Asp Asp Ser Gln Ala Ser Arg Asn Leu Val Tyr Val
        355                 360                 365

Leu Leu Leu Ala Ala Asn Leu Asn Asp Val Met Cys Ser Gly Gly Asp
    370                 375                 380

Tyr Ser Phe Ala Leu Pro Val Pro Gln Trp Pro Val Ile Lys Pro Gly
385                 390                 395                 400

Thr Val Thr Leu His Thr Ala Gly Val Thr Leu Ser Thr Gln Phe Thr
                405                 410                 415

Asp Phe Val Ser Leu Asn Ser Leu Arg Phe Arg Phe Arg Leu Ala Val
            420                 425                 430

Glu Glu Pro Ser Phe Thr Ile Thr Arg Thr Arg Val Ser Lys Pro Tyr
        435                 440                 445

Gly Leu Pro Ala Ala Asn Pro Asn Gly Gly Lys Glu Ser Tyr Glu Val
    450                 455                 460

Ala Gly Arg Phe Pro Phe Asn Ser Leu Val Pro Ser Asn Asp Asp Tyr
465                 470                 475                 480

Pro Thr Pro Ile Thr Asn Ser Val Thr Val Arg Gln Ala Leu Glu Arg
                485                 490                 495

Arg Leu Asn Glu Ser Arg Glu Glu Phe Asn Asn Leu Ser Gln Glu Thr
            500                 505                 510

Ala Val Ser Gln Leu Ile Asp Leu Ala Met Trp Pro Leu Asp Met Phe
        515                 520                 525

Pro Met Phe Ser Glu Ile Glu Ser Thr Val Ile Ala Ala Lys Pro Met
    530                 535                 540

Ala Thr Asn Val Met Arg Lys Leu Lys Ser Ser Lys Leu Ala Ser Pro
545                 550                 555                 560

Val Ser Met Leu Ser Asp Ser Leu Ser Asp Ala Ala Tyr Ser Ile Ala
                565                 570                 575

Arg Ser Thr Pro Val Arg Ser Ile Gly Pro Thr Ala Ser Arg Trp Ala
            580                 585                 590

Asn Ile Pro Glu Gln Thr Gln Asp Ala Val Ser Glu Val Ala Thr Ile
        595                 600                 605

Ser Ser Gln Val Ser Gln Ile Ser Pro Lys Leu Arg Leu Lys Glu Ile
    610                 615                 620

Pro Thr Pro Thr Glu Gly Leu Asn Phe Asp Asp Ile Ser Arg Arg Tyr
625                 630                 635                 640

Ser Lys Ala Lys Ile Glu Arg Ser Ile Gln Val Ala Pro Asn Ala Leu
                645                 650                 655

Pro Asp Val Ile Thr Glu Ala Ser Glu Lys Phe Ile Arg Asn Arg Ala
            660                 665                 670

Tyr Arg Val Ile Asp Gly Asp Glu Ala Phe Glu Ala Gly Thr Asp Gly
        675                 680                 685

Arg Phe Phe Ala Tyr Arg Val Glu Thr Leu Glu Glu Met Pro Phe Asn
    690                 695                 700

Ile Glu Lys Phe Ala Asp Leu Val Thr Asn Ser Pro Val Ile Ser Ala
705                 710                 715                 720
```

-continued

```
Ile Ile Asp Phe Lys Thr Leu Lys Asn Leu Asn Asp Asn Tyr Gly Ile
                725                 730                 735

Thr Arg Glu Gln Ala Phe Ser Leu Leu Arg Ser Asp Pro Lys Val Leu
            740                 745                 750

Arg Gly Phe Ile Ala Gln Asn Asn Pro Ile Ile Lys Asn Arg Ile Glu
        755                 760                 765

Gln Leu Ile Met Gln Cys Arg Leu
    770                 775


<210> SEQ ID NO 42
<211> LENGTH: 18
<212> TYPE: DNA
<213> ORGANISM: Bovine rotavirus

<400> SEQUENCE: 42

gaccaggtcg ccccactg                                                   18


<210> SEQ ID NO 43
<211> LENGTH: 19
<212> TYPE: DNA
<213> ORGANISM: Bovine rotavirus

<400> SEQUENCE: 43

agtataagta ttaaaattc                                                  19


<210> SEQ ID NO 44
<211> LENGTH: 18
<212> TYPE: DNA
<213> ORGANISM: Bovine rotavirus

<400> SEQUENCE: 44

gtaagaattt cgaacttg                                                   18


<210> SEQ ID NO 45
<211> LENGTH: 20
<212> TYPE: DNA
<213> ORGANISM: Bovine rotavirus

<400> SEQUENCE: 45

agccacatga tcttgtttac                                                 20


<210> SEQ ID NO 46
<211> LENGTH: 18
<212> TYPE: DNA
<213> ORGANISM: Bovine rotavirus

<400> SEQUENCE: 46

cccgtcgacg aattcttt                                                   18


<210> SEQ ID NO 47
<211> LENGTH: 24
<212> TYPE: DNA
<213> ORGANISM: Bovine rotavirus

<400> SEQUENCE: 47

tttactgttt tcgtaacagt tttg                                            24


<210> SEQ ID NO 48
<211> LENGTH: 21
<212> TYPE: DNA
<213> ORGANISM: Bovine rotavirus
```

-continued

```
<400> SEQUENCE: 48

caacaacgca cagaatctag c                                               21


<210> SEQ ID NO 49
<211> LENGTH: 18
<212> TYPE: DNA
<213> ORGANISM: Bovine rotavirus

<400> SEQUENCE: 49

aaatgataac catctcga                                                   18


<210> SEQ ID NO 50
<211> LENGTH: 15
<212> TYPE: DNA
<213> ORGANISM: Bovine rotavirus

<400> SEQUENCE: 50

gtccaagttt ccctg                                                      15
```